(12) United States Patent
Ahmed et al.

(10) Patent No.: US 8,153,613 B2
(45) Date of Patent: Apr. 10, 2012

(54) BARRIER FILM-FORMING GERMICIDAL COMPOSITION FOR CONTROLLING MASTITIS

(75) Inventors: Fahim U. Ahmed, Greensboro, NC (US); N. Camelia Traistaru, Kansas City, MO (US); Lieven Uytterhaegen, Drongen (BE)

(73) Assignee: DeLaval Holding AB, Tumba (SE)

( * ) Notice: Subject to any disclaimer, the term of this patent is extended or adjusted under 35 U.S.C. 154(b) by 1029 days.

(21) Appl. No.: 11/439,941

(22) Filed: May 24, 2006

(65) Prior Publication Data

US 2007/0275070 A1    Nov. 29, 2007

(51) Int. Cl.
*A61K 31/721* (2006.01)
*A61K 31/715* (2006.01)
*A01N 25/00* (2006.01)

(52) U.S. Cl. .......... 514/58; 424/404; 424/405; 424/407; 514/54

(58) Field of Classification Search ................ 424/406, 424/407, 401, 404, 405; 514/58, 54
See application file for complete search history.

(56) References Cited

U.S. PATENT DOCUMENTS

| 4,113,854 A * | 9/1978 | Andrews et al. ........... 424/78.05 |
| 5,063,249 A | 11/1991 | Andrews |
| 5,139,771 A | 8/1992 | Gerstein |
| 5,776,479 A | 7/1998 | Pallos et al. |
| 6,030,633 A | 2/2000 | Hemling et al. |
| 6,046,178 A * | 4/2000 | Silvetti, Sr. .................... 514/60 |
| 2007/0077235 A1 | 4/2007 | Loomis et al. |

FOREIGN PATENT DOCUMENTS

| DE | 19627498 | 1/1998 |
| EP | 896521 B1 | 11/1997 |
| EP | 1080714 | 3/2001 |
| WO | WO 2007/050700 | 5/2007 |

OTHER PUBLICATIONS

PCT/US2007/069677 International Search Report & Written Opinion mailed Nov. 6, 2007, 13 pages.
European Application No. 07 784 116.1 Communication pursuant to Article 94(3) EPC Nov. 24, 2009, 4 pages.

* cited by examiner

*Primary Examiner* — Gina C Yu
(74) *Attorney, Agent, or Firm* — Hovey Williams LLP

(57) ABSTRACT

A long-lasting persistent, uniform film-forming skin protecting germicidal composition provides a long-lasting persistent barrier film when applied to skin. The compositions have particular utility as barrier teat dips for protecting cows against mastitis. A barrier film-forming agent is selected from the modified or hydrolyzed polysaccharides, particularly a hydrolyzed or modified starch, such as dextrin and maltodextrin. The barrier film-forming agent is stably solubilized in a solvent that dries to form the long-lasting persistent uniform film over the animal skin. The compositions also contain antimicrobial agents that fight against microbes that manage to penetrate the protective barrier film. Particularly, advantageous is that all the materials used are safe food additive and cost effective over the traditional barrier film forming agents.

18 Claims, 1 Drawing Sheet

BARRIER FILM-FORMING GERMICIDAL COMPOSITION FOR CONTROLLING MASTITIS

BACKGROUND

I. Field of the Invention

The present invention relates to compositions and methods for controlling mastitis in animals. More particularly, a modified polysaccharide based composition forms a barrier film that is useful in protecting the teats of dairy animals from microbial infections of the milk channels. The barrier efficacy may be further enhanced by inclusion of germicidal or antimicrobial agents.

II. Description of the Related Art

One major cause of economic loss for dairy farmers is the incidence of mastitis in cows or dairy animals. Overall annual economic losses due to mastitis approximate $185 per dairy animal. This totals to approximately $1.7 billion annually for the entire United States market.

Mastitis is typically caused by infection of the milk ducts by microorganisms. Severe cases of mastitis may cause death of the dairy animals. Milder cases of mastitis are more common, and may result in loss of milk production together with an increased cost of veterinary care for the dairy farmer.

Dairy farmers have traditionally taken two approaches to prevent the cows from contracting mastitis. Antimicrobial compositions may be used to reduce the risk of infection. One measure employs germicidal agents to kill the microbes. The other approach uses a persistent film-forming composition that is applied to the bovine teats as a barrier to block the microbes from entering the milk ducts.

Despite intensive research and testing for an ideal composition that can effectively protect the animals from mastitis, many problems persist. Although many compositions can form a layer of film over the teat skin, the film tends to crack during drying, leaving some areas of teat skin unprotected. Some compositions form a layer of film over the skin that is too easily washed off when in contact with dung, mud or water. Other materials cannot be removed easily enough, and may be a source of contamination that complicates the milking and milk purification process. Moreover, some film-forming components are incompatible with the germicide and other ingredients essential for formulations, resulting in a reduced potency of the germicide. It is difficult to formulate a protective film that is continuous, uniform, non-brittle, persists 8-12 hours on the teat between milkings, mild on skin, easily removed by cleaning prior to milking and is non dripping when applied.

U.S. Pat. No. 5,063,249 issued to Andrews describes a teat dip containing dodecylaminolkylamine derivatives, an emollient and Poly(N-VinylPyrrolidone) (or "PVP") as a film-forming ingredient. However, the teat dip described in this patent is highly fluid and, consequently, is less likely to adhere to the teat skin as the formulation is not able to vertically cling onto teats with sufficient strength to form a long-lasting protective film. Furthermore, due to low viscosity and dripping, the product does not form a persistent protective film.

Another type of barrier utilizes cellulose as a barrier-forming agent. U.S. Pat. No. 5,776,479 issued to Pallos et. al. discloses a germicidal teat dip composition that contains a film-forming ingredient selected from the group consisting of hydroxyethylcellulose, methylhydroxypropylcellulose and ethylhydroxyethylcellulose. The composition also includes a germicidal agent, such as iodine, which complexed with a nonionic surfactant and water to provide a solution having a viscosity of from about 50 to 1000 cPs. After being applied to the teats of agricultural animals, the liquid dries to form a continuous barrier film.

EP 896,521 B1 describes a barrier-forming mixture that uses a longer chain polysaccharide derivative, such as methylcellulose or hydroxyethylcellulose that is present in an amount ranging from 10% to 20% of the composition by weight. The efficacy of this polysaccharide material is enhanced by the use of a low molecular weight saccharide material that may be, for example, a monosaccharide or disaccharide and may include hydrolyzed starches, such as maltodextrin. Although the polysaccharide material and the saccharide material are not exceptionally effective alone, a synergistic effect is achieved when the materials are used in combination such that the low molecular weight synergistic saccharide is present in an amount ranging from 2% to 10% of the composition by weight, or roughly 20% to 50% of the amount of polysaccharide.

The use of polysaccharide based cellulose and cellulose derivatives in teat dip compositions present a number of problems. The solutions tend to drip after application to the teats, and a certain amount of product is wasted. The dripping of the applied solutions also results in a thinner barrier film than is not ideal for use on dairy animals. It is difficult to formulate quick-drying compositions because cellulose is relatively insoluble in commonly used volatile solvents, such as short chain alcohols.

U.S. Pat. No. 6,030,633 issued to Hemling et al. describes a film-forming composition to protect dairy animals from contracting mastitis during the dry period of the dairy animals. The composition includes a film-forming component such as a mixture of polyether, polyurethane and benzoin gum, which is dispersed in a compatible carrier and forms an elastic barrier film when applied on the skin. The composition also contains a small amount of nitrocellulose, in order to enhance the adherence of the film to the skin. The composition further includes a germicide to kill microorganisms that break the physical barrier.

Although polysaccharides such as hydroxypropyl cellulose, methyl cellulose, hydroxypropyl methyl cellulose and non-polysaccharides such as polyvinylpyrrolidone, etc. are typically used in combination with film barrier agents in aqueous film coating, when used alone they often produce inferior film on teats. Moreover, these ingredients are expensive. Although, polysaccharides may assist the formation of high quality films when used in combination with other film forming agents, formulators are constantly looking for more efficient, better alternatives to enhance coatings or lower overall cost of the coatings.

Much progress has been made in preventing the incidence of mastitis, but there remains a need for a composition that is not only germicidically effective but also forms a long-lasting persistent, continuous, uniform film as a physical barrier between the animal skin and microorganisms in the environment. A need also exists for such films to be easily removed so as not to contaminate milk, while also lasting long enough to protect from bacteria in between milking. The duration of film coverage is normally 8 to 12 hours, but may occasionally be as long as 24 hours.

SUMMARY

The present disclosure overcomes the problems outlined above and advances the art by providing compositions that are capable of forming a long-lasting persistent, continuous, uniform barrier film that is based upon modified polysaccharides when applied to the skin. The compositions have particular utility as barrier teat dips that are used prophylactically against mastitis. The barrier film-forming agent includes relatively low molecular weight polysaccharides, for example, as may be derived specifically from hydrolyzed starch.

The composition may be used for prophylactic treatment of a dairy animal's teats to provide a long lasting persistent protective germicidal barrier film that demonstrates persistence between milkings, and is controllably reproducible to yield a continuous, uniform persistent barrier. This treatment process entails milking the animal, coating the teats with the composition after milking, allowing the composition to dry and so also form a layer of persistent barrier film on the teats. The composition may be applied topically by painting, foaming, dipping or spraying. Furthermore, use of the composition is not limited to use against mastitis, and the composition may be used generally to treat or protect against any infectious skin condition.

A composition capable of forming a long-lasting, persistent, continuous, uniform barrier film may contain from about 0.1% to about 20% by weight of modified or hydrolyzed polysaccharide material for use as the barrier forming agent. The polysaccharide material has a majority polysaccharide component as starch, modified starch, hydrolyzed starch, a starch derivative, and combinations thereof. The majority polysaccharide components may have overall or average Dextrose Equivalence (DE) value ranging from 2 to 50, and this value more preferably ranges from 3 to 27. In this sense the term "majority polysaccharide component" is used to describe a majority weight percentage of all polysaccharides in the composition, i.e., more than 50% of all polysaccharides in the composition.

In one aspect, the teat dip composition may be described as a homogenous mixture including:
a) from about 0.1% to about 20% by weight of a modified polysaccharide barrier film-forming agent;
b) from about 0.1% to about 20% by weight of an antimicrobial agent or synergistically optimized mixture of antimicrobial agents;
c) at least one thickening agent, as needed, that is effective to produce a viscosity of from 50-4000 cPs; and
(d) at least one solvent.

Preferred formulations may also contain compatible additives to condition the skin and to improve the surface activity of the composition, such as:
(e) from 0.1% to 20% by weight of at least one emollient and skin conditioning agent,
(f) from 0.1% to 5% of at least one surface active or wetting agent.

As described below, the use of starch or modified starch polysaccharides of suitable Dextrose Equivalence (DE) value to form a barrier material in teat dip formulations is a significant advance in the art. In particularly preferred formulations, the majority polysaccharide component is present in an amount comprising at least 0.1% of the composition weight, and even more preferably this is at least 1%.

The majority polysaccharide component may be starch, hydrolyzed starch or modified starch, for example, dextrin, maltodextrin, and combinations thereof. In other aspects, the entire amount of polysaccharide material may consist essentially of the majority polysaccharide component diluted with less than one or two percent of such longer chain polysaccharides as cellulose or modified cellulose by weight of the composition. Alternatively, the total amount of polysaccharide material may contain a minority amount of such longer chain polysaccharides as cellulose or modified cellulose component.

The barrier functionality is only one way to provide prophylactic benefit against mastitis. It will be appreciated that supplementation with antimicrobial or germicidal active agents provides additional benefit. The persistent, continuous, uniform barrier material is advantageously compatible with most known antimicrobial active agents. These may be used individually or in combination, for example, such as chlorohexidine digluconate, chlorohexidine diacetate, lactic acid, benzyl alcohol, lower alkanols ($C_1$-$C_4$), organic acids, salicylic acid and mixtures thereof. Other antimicrobial agents may include, for example, organic peroxide, hydrogen peroxide, peroxy acids and mixtures thereof. Still other antimicrobial agents may include bronopol (2-bromo-2-nitro-1, 3-propanediol), lactic acid, aliphatic carboxylic acid ($C_4$-$C_{10}$), dodecylbenzenesulfonic acid, benzyl alcohol, salicylic acid and mixtures thereof in various combinations or groups. Another instance of antimicrobial agents that may be used singularly or in combination includes Ventocil® a polyhexamethylenebiguamide [poly(iminoimidocarbonyliminidocarbonyliminohexamethylene)hydrochloride] from Avecia, chlorohexidine a cationic polymeric bisbiguamide [1,6-di(4-chlorophenyl-diguamido)hexane derivative, lactic acid, benzyl alcohol, salicylic acid and mixtures thereof. Alternatively, another such group is quaternary ammonium compounds, lactic acid, benzyl alcohol, salicylic acid and mixtures thereof. Another example of this is chlorine dioxide, hypohalous acid, alkali hypohalites, alkyl and aryl chlorosulfamates and mixtures thereof.

Although some embodiments may find particular advantage by selecting from among the above groupings, it will also be appreciated that use of the foregoing antimicrobial active agents is not limited to the above groupings, that a number of additional antimicrobial agents are well known in the art, and the functional benefit may be broadly achieved by choosing one or more of these materials in any combination.

One object of the disclosed instrumentalities is to provide a biocidal and persistent barrier film-forming composition that may be used for prevention of mastitis. In one embodiment, the composition may be applied to the skin of animal teats to form a biocidal layer of persistent continuous, uniform film covering the skin. In another embodiment, the composition may be used as a teat dip. In other embodiments, the composition may also be used as a hand sanitizer, a skin cleanser, a surgical scrub, a wound care agent, a disinfectant, a hard surface sanitizer and the like. Preferred compositions for skin applications have a pH of about 2.0 to about 9.0 and provide a substantial reduction, e.g., greater than 99% or preferably 99.999% of Gram positive and Gram negative bacterial populations.

In another aspect, the aforementioned composition may be supplemented by buffering agents, pH adjusting agents, emollients, preservatives, a moisturizing agents, skin conditioning agents, surfactants or wetting agents, viscosity control agents, colorants, opacifying agents and combinations thereof. These may be present in any suitable amount. Generally, the colorant constitutes from 0.001% to about 5.00% (w/w), and the emollient or skin conditioning agent from 1% to 30% (w/w) of the composition.

Viscosity control is a particular consideration for any intended environment of use. Viscosity of the composition may contain a viscosity modifier to provide a viscosity of any value, but preferably ranging from 1 cPs to 4000 cPs at ambient temperature. The viscosity referred throughout in this application is Brookfield viscosity measured in cPs unit by a Brookfield LV viscometer at ambient temperature (25° C.) with a spindle #2@30 rpm. In various embodiments, a thickener such as a non-cellulosic thickener, may be added to achieve a viscosity range of from 50 cPs to 4000 cPs, or from 100 cPs to 2000 cPs to facilitate proper barrier film formation and ease of application for various dairy needs without excessive product loss through dripping. This may be done, for example, by adding from 0.01% to 15% (w/w) of a viscosity modifier or thickener such as the block copolymers of ethylene oxide commonly known as Pluronic gels or Poloxamers.

Conventional thickeners include such plant gum materials as guar gum; starch and starch derivatives, for example hydroxyethyl starch or cross-linked starch; microbial polysaccharides, for example xanthan gum, sea weed polysaccharides, for example sodium alginate, carrageenan, curdlan, pullulan or dextran, dextran sulfate, whey, gelatin, chitosan, chitosan derivatives, polysulfonic acids and their salts, polyacrylamide, and glycerol. Cellulosic thickeners may be used including hemicellulose, for example arabinoxylanes and glucomannanes; cellulose and derivatives thereof, for example methyl cellulose, ethyl cellulose, hydroxyethyl cellulose or carboxymethyl cellulose. The cellulosic thickeners form part of the total amount of polysaccharide material and are preferably used in amounts that do not exceed the preferably do not exceed the majority component of polysaccharide material having the Dextrose Equivalence (DE) value ranging from 2 to 50 as described above.

Another consideration is pH, where a preferred pH range for the composition is from 1.5 to 10, more preferably 2.0 to about 9.0. Generally, the pH may be adjusted by the addition of acid or base or buffer to any value that is desired in the intended environment of use.

The composition is prepared by combining aqueous thickened liquid formulations containing the organic components to form a smooth viscous material that may be applied onto teats of target animals as a prophylactic measure against mastitis. Mixtures prepared according to the disclosed composition exhibit excellent chemical and rheological stability, as well as a strong clinging capacity to immobilize the persistent, continuous, uniform barrier film on animal teat surfaces. Thus, in one aspect this improved composition provides long-term persistence and protection from mastitis without causing dermal irritations.

In one aspect, the composition may form a non-dripping and long lasting, persistent, prophylactic, continuous, uniform barrier film when applied to animal teats, thus providing physical protection against microbial infection between milkings. Because a small amount of the barrier film may inevitably get into the milk product, the preferred composition disclosed herein is particularly advantageous in that all the components are generally recognized as safe for human consumption (or "GRAS") or are approved as direct or indirect food additives. Another aspect of the composition is that a sensory panel taste conducted by an independent organization though a group of expert panels concluded that they could not detect any foreign taste from the materials of the composition in milk up to a concentration of 1% compared to traditional iodine based commercial products which tested and perceived to have detectable foreign ingredients.

By contrast to conventional films that use PVP, the composition disclosed herein employs a hydrolyzed or modified starch material, such as maltodextrin, as a barrier film-forming agent which provides much stronger adhesion to the substrate, faster drying and improved persistence and retention on animal teats. Thus, none or very little film-forming product is wasted and significant product and labor cost associated with re-application of the film is saved.

In other aspects, the disclosed composition may also contain germicidal agents that may kill bacteria, yeast and other microorganisms. The unique antimicrobial formulations that are stable over an extended period of time afford more effective microbial control in between milkings as compared to previously disclosed compositions.

DETAILED DESCRIPTION

Figure 1:
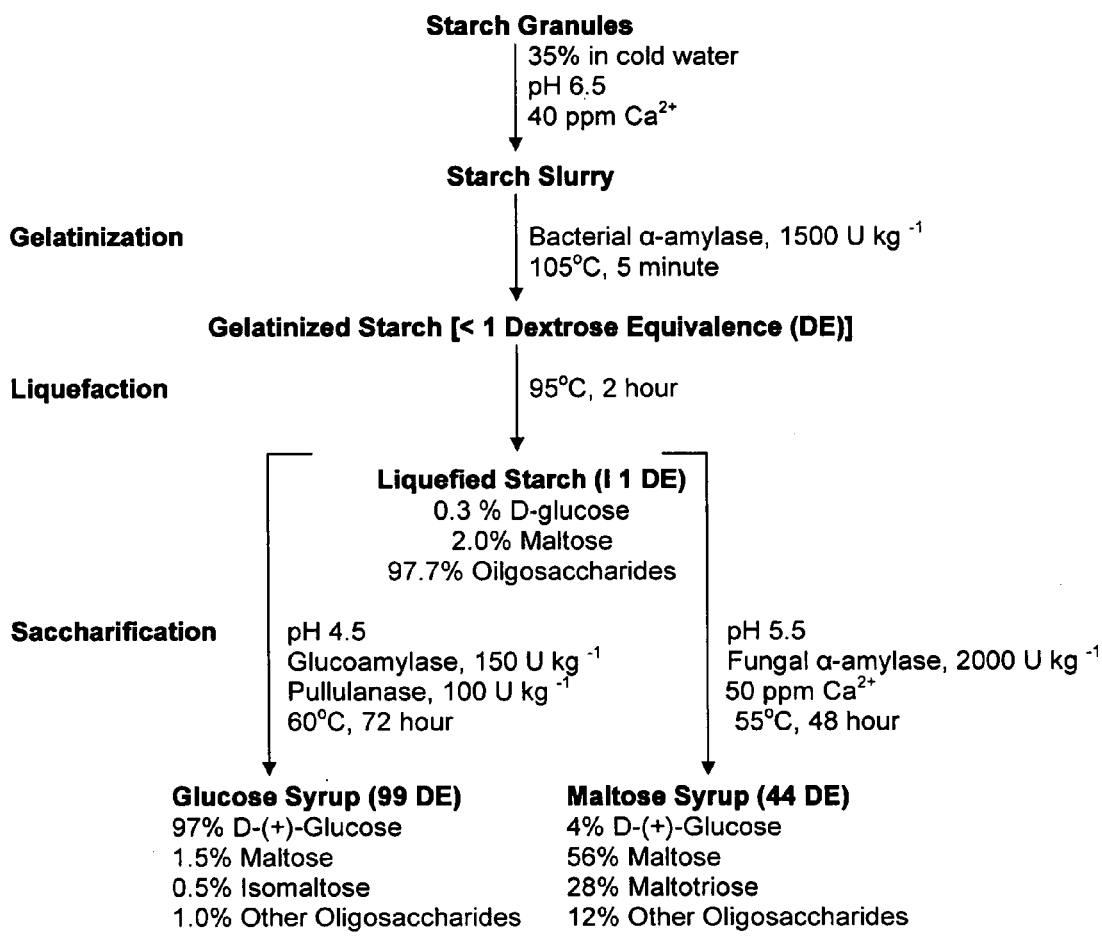
FIG. 1 is a typical commercial process diagram showing the hydrolysis of starch to produce various low molecular weight grades of hydrolyzed starch.

There will now be shown and described an improved composition and method that effectively protect mammals from mastitis. The composition may form a continuous, uniform, long-lasting persistent film over the animal teats. This barrier film protects the skin from physical exposure to microbes in the environment. The composition also contains antimicrobial agents that may kill bacteria and other microorganisms which have broken the physical barrier and enter into teat canals.

The barrier forming materials described herein are primarily modified polysaccharides, but these may also be used in combination with other barrier forming materials, such as PVP. The preferred barrier forming material is hydrolyzed or modified polysaccharide material from about 0.1% to about 20% by weight of the composition. The polysaccharide material has a majority amount of polysaccharide component selected from the group consisting of starch, hydrolyzed starch, modified starch, a starch derivative, and combinations thereof. The majority amount of modified or hydrolyzed polysaccharide component has overall Dextrose Equivalence (DE) value ranging from 2 to 50, and preferably from 3 to 27.

In one aspect, the film-forming agents may form a thin, continuous, persistent, uniform layer of barrier film over the skin of the animal's teats, and may be applied by dipping, foaming or spraying onto the teats. The barrier film-forming agents useful for the present disclosure include modified or hydrolyzed polysaccharide derivatives of relatively low molecular weight. Preferably, the modified or hydrolyzed polysaccharide derivatives are polymers composed of less than about 1000 monosaccharide units.

Polysaccharide Materials

Modified or hydrolyzed polysaccharide in the present disclosure refers to polymers made up of many monosaccharide units joined together by glycoside linkages. Polysaccharides are generally represented by the formula $C_n(H_2O)_{n-1}$, wherein n is typically number greater than 200. Modified or hydrolyzed polysaccharides are products that result from hydrolysis by acids or enzymes to lower molecular weight fractions. Polysaccharide derivatives are products that result from chemical modification or hydrolysis of polysaccharides.

Thus, the term modified or hydrolyzed polysaccharide or polysaccharide derivative encompasses molecules over a wide range of molecular weight. For instance, hydrolysis of starch to a different extent results in carbohydrates of different chain length of D-(+)-glucose units, with glucose being the product of complete hydrolysis. Thus, polysaccharide derivatives may include molecules that have as their backbones a monosaccharide, a disaccharide, an oligosaccharide, or a polysaccharide. As used herein, the term "low molecular weight polysaccharide material" refers to a hydrolyzed or modified polysaccharide or polysaccharide derivative having a molecular weight ranging from about 2 D-(+)-glucose units to about 500 D-(+)-glucose units.

As is known in the art, the various types of polysaccharides are differentiated into different classes, varieties and grades. Polysaccharides are compounds which are made up of many hundreds- or even thousands-monosaccharide units per molecule. Polysaccharides are naturally occurring polymers. By far the most important polysaccharides are cellulose and starch. Both are produced in plants from carbon dioxide and water by the process of photosynthesis and both are made up of D-(+)-glucose units. Cellulose is the chief structural material of plants, giving the plants rigidity and form. Starch makes up the reserve food supply of plants and occurs chiefly in seeds. Starch is more water-soluble than cellulose and is easily hydrolyzed. Cellulose is used for its structural properties: as wood for houses, furniture; as cotton or rayon for clothing; as paper for communication and packaging. Starch is used as food: potatoes, corn, rice, wheat etc.

Cellulose is the chief component of wood and plant fibers; cotton for instance is the purest natural form of cellulose containing about 90% cellulose. Rayon is a form of regenerated cellulose. Cellulose is practically insoluble in water or other usual solvents. Cellulose is a polysaccharide and is generally represented by $(C_6H_{10}O_5)_n$ with the D-(+)-glucose units linked as in dimeric cellobiose. Cellobiose, ($C_{12}H_{22}O_{11}$, molecular weight 342.30) is a repeating unit of cellulose and lichenin and is joined by two D-(+)-glucose units linked at C-4 by a β-linkage. A fibrous form of cellulose is the basic material for the textile and paper industries, and is also used in food industry as stabilizer, thickener and texturizer. Formula I shows the generalized structure of the cellulose linkages and repeating glucose units lose also precipitates at elevated temperature 40-45° C. making it unsuitable for use at this temperature. Like starch, cellulose is made of chains of D-(+)-glucose units, each unit is joined by a glycoside linkage to C-4 of the next but it differs from starch however, in the configuration of the glycoside linkage in cellulose. Formula (II) illustrates this by way of example where (+)-cellubiose has a β-linkage, whereas, starch has an α-linkage:

Formula (II):

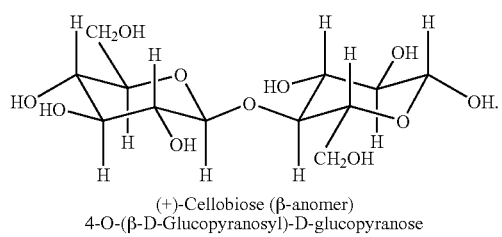

(+)-Cellobiose (β-anomer)
4-O-(β-D-Glucopyranosyl)-D-glucopyranose

In general, starch occurs in the form of white granules, usually made up of about 20% of water-soluble linear polymer fraction called amylose and 80% of water insoluble branched polymer fraction called amylopectin. The granules are organized mixtures of the two types of polymers so oriented and associated in a crystal like lattice that they are insoluble in cold water and are comparatively resistant to naturally occurring hydrolytic agents such as enzymes. These two fractions appear to correspond to different carbohydrates of higher molecular weight and formula is generally represented by $(C_6H_{10}O_5)_n$ where n may be greater than one thousand. Most varieties of starch contain these two types of polymers which differ from each other in molecular weight and in chemical structure.

The linear polymer amylose consists of 200-1000 glucopyranose units joined to each other through α-1,4-glucosidic linkages, whereas the branched or ramified polymer, amylopectin, is made up of 1500 or more glucopyranose units. In addition to the normal or predominating α-1,4-glucosidic linkages, an anomalous α-1,6-glucosidic is present in the ramified structure at the origin or point of branching in a ratio of about 1:25. Upon treatment with acid or under the influence of enzymes, the components of starch are hydrolyzed Formula (I):

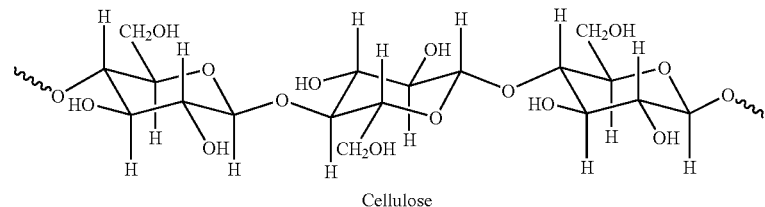

Cellulose

Derivatives of cellulose materials such as hydroxypropylcellulose, hydroxyethyl cellulose, hydroxymethyl cellulose, and hydroxypropylmethyl cellulose are widely used as thickeners and film-forming barrier agents either alone or in combination with other co-thickeners/barrier agents. Carboxymethyl cellulose (CMC) is a well known cellulose gum, but it has limited suitability for use as it is unstable below pH of 5 and it precipitates at pH values near 3. Hydroxypropyl celluprogressively to dextrin which is a mixture of low molecular weight polysaccharides, (+)-maltose and finally to D-(+)-glucose. A mixture of all these is found in corn syrup. Both amylose and amylopectin are made up of D-(+)-glucose units, but differ in molecular size and shape. Amylopectin has a highly branched structure and amylase has little or no branching. Formula (III) shows the structure for amylose and Formula (IV) the structure for amylopectin.

Formula (III)

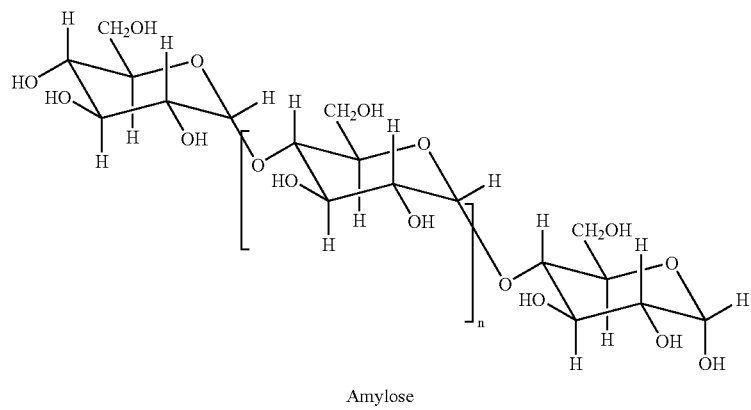
Amylose

Formula (IV)

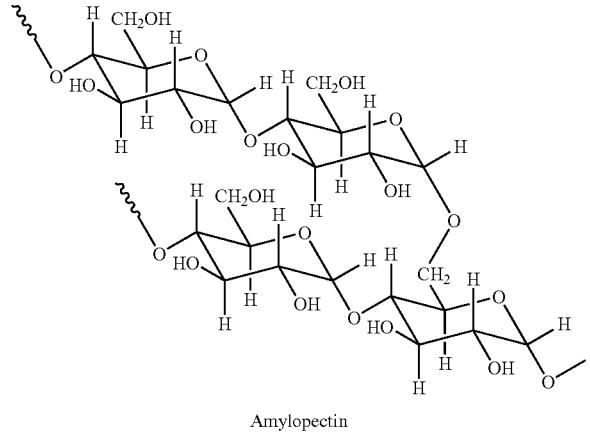
Amylopectin
(chair conformations assumed)

Maltose, a dimmer of D-(+)-glucose that is joined by α-linkage is a repeating unit in starch. Maltose is a disaccharide of two D-(+)-glucose units linked at C-4 through α-linkage and is a hydrolyzed product of amylose. Amylose is believed to be made up of long chains, each containing 1000 or more D-(+)-glucose units joined together by α-linkages as in (+)-maltose. Amylose is the fraction of starch that gives the intense blue color with iodine. Amylopectin is hydrolyzed to the single disaccharide (+)-maltose as shown in Formula (V).

Formula (V):

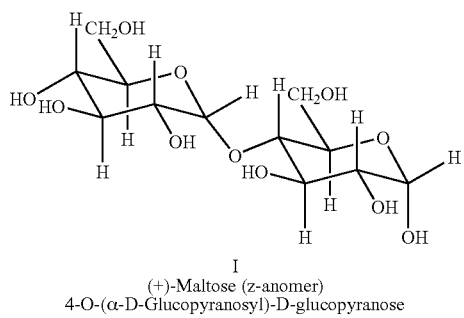
I
(+)-Maltose (z-anomer)
4-O-(α-D-Glucopyranosyl)-D-glucopyranose

One preferred film-forming agent according to the present instrumentalities is a partially hydrolyzed or modified starch, such as dextrin and/or maltodextrin. Dextrin is a polysaccharide material that is produced by the dry heating of unmodified starches, as well as enzymatic or acid-catalyzed hydrolysis of wet starch. Dextrin used as an excipient for dry extracts and pills, for preparing emulsions, for thickening dye pastes, sizing paper and fabrics. Maltodextrins are non sweet nutritive saccharide polymers that consist of D-(+)-glucose units linked primarily by α-(C1-C4) bonds and are prepared by the partial hydrolysis of corn starch by acids or enzymes into smaller chains of such bonds, such as 3-20 chains in maltodextrin. Dextrin sub-categorized into different grades including a number of nutritional additives and materials that and are commonly used for tableting pharmaceuticals. These dextrins are usually mixtures of D-(+)-glucose polymers that are often produced by controlled hydrolysis of corn starch. They are most often categorized by Dextrose Equivalence (DE) value, which is a well known unit of measurement in the starch industry. Dextrose Equivalence (DE) is the inverse of the Degree of Polymerization (DP) and the most commonly applied quantitative measurement of starch polymer hydrolysis. For example, the total hydrolysis that starch can convert to dextrose (D-(+)-glucose) is 100%. Thus, the Dextrose Equivalence (DE) of D-(+)-glucose is 100 and Dextrose Equivalence (DE) is a measure of reducing power compared to a dextrose standard of 100. The higher the Dextrose Equivalence (DE), the greater is the extent of starch hydrolysis, resulting in a smaller average polymer size.

Acid hydrolysis of starch has seen widespread use in the past, but is now largely replaced by enzymatic processes. FIG. 1 is a flow chart outlines a prior art use of enzymes in a typical commercial process for the hydrolysis of starch that is useful in producing hydrolyzed or modified polysaccharide materials that may be used according to the description as shown below.

Of the two components of starch, amylopectin presents the great challenge to hydrolytic enzyme systems. This is due to the residues involved in α-1,6-glycosidic branch points which constitute about 4-6% of the D-(+)-glucose present. Most hydrolytic enzymes are specific for α-1,4-glucosidic links yet the α-1,6-glucosidic links must also be cleaved for complete hydrolysis of amylopectin to D-(+)-glucose. Some of the most impressive recent exercises in the development of new enzymes have concerned debranching enzymes.

As represented in FIG. 1, starch hydrolysis processes may be condensed into two broad classes: (1) processes in which the starch hydrolysate is to be used by microbes or man and (2) processes in which it is necessary to eliminate starch. In the former processes, such as D-(+)-glucose syrup production, starch is usually the major component of reaction mixtures, whereas in the latter processes, such as the processing of sugar cane juice, small amounts of starch which contaminate non-starchy materials are removed. Enzymes of various types are used in these processes. Although starches from diverse plants may be utilized, corn is the world's most abundant source and provides most of the substrate used in the preparation of starch hydrolysates.

There are three stages in the conversion of starch:
1. gelatinization, involving the dissolution of the nanogram-sized starch granules to form a viscous suspension;
2. liquefaction, involving the partial hydrolysis of the starch, with concomitant loss in viscosity; and
3. saccharification, involving the production of D-(+)-glucose and maltose by further hydrolysis.

Gelatinization is achieved by heating starch with water, and occurs necessarily and naturally when starchy foods are cooked. Gelatinized starch is readily liquefied by partial hydrolysis with enzymes or acids and saccharified by further acidic or enzymatic hydrolysis.

The starch and D-(+)-glucose syrup industry uses the expression Dextrose Equivalence (DE), similar in definition to the Degree of Hydrolysis (DH) units of proteolysis, to describe its products, where:

$$\text{Dextrose Equivalence}(DE) = 100 \times \left( \frac{\text{Number of Glycosidic Bonds Cleaved}}{\text{Initial Number of Glycosidic Bonds Present}} \right) \quad \text{(VI)}$$

In practice, this is usually determined analytically and closely approximated by use of the expression:

$$\text{Dextrose Equivalence}(DE) = 100 \times \left( \frac{\text{Reducing Sugar, Expressed as } D\text{-}(+)\text{-Glucose}}{\text{Total Carbohydrate}} \right) \quad \text{(VII)}$$

Thus, Dextrose Equivalence (DE) represents the percentage hydrolysis of the glycoside linkages present. Pure D-(+)-glucose has a Dextrose Equivalence (DE) of 100, pure maltose has a Dextrose Equivalence (DE) of about 50 and starch has a Dextrose Equivalence (DE) of effectively zero. During starch hydrolysis, Dextrose Equivalence (DE) indicates the extent to which the starch has been cleaved. Acid hydrolysis of starch has long been used to produce 'glucose syrups' and even crystalline D-(+)-glucose (dextrose monohydrate). Very considerable amounts of 42 DE syrups are produced using acid and are used in many applications in confectionery. Further hydrolysis using acid is not satisfactory because of undesirably colored and flavored breakdown products. Acid hydrolysis appears to be a totally random process which is not influenced by the presence of α-1,6-glucosidic linkages. For these reasons, enzymatic hydrolysis is often preferred. Table 1 provides a number of enzymes that are in commercial use for this purpose.

TABLE 1

Common Enzymes used in Starch Hydrolysis

| Enzyme | EC number | Source | Action |
| --- | --- | --- | --- |
| α-Amylase | 3.2.1.1 | Bacillus amyloliquefaciens | Only α-1,4-oligosaccharide links are cleaved to give α-dextrins and predominantly maltose (G2), G3, G6 and G7 oligosaccharides |
|  |  | B. licheniformis | Only α-1,4-oligosaccharide links are cleaved to give α-dextrins and predominantly maltose, G3, G4 and G5 oligosaccharides |
|  |  | Aspergillus oryzae, A. niger | Only α-1,4 oligosaccharide links are cleaved to give α-dextrins and predominantly maltose and G3 oligosaccharides |
| Saccharifying α-amylase | 3.2.1.1 | B. subtilis (amylosacchariticus) | Only α-1,4-oligosaccharide links are cleaved to give α-dextrins with maltose, G3, G4 and up to 50% (w/w) glucose |
| β-Amylase | 3.2.1.2 | Malted barley | Only α-1,4-links are cleaved, from non-reducing ends, to give limit dextrins and β-maltose |
| Glucoamylase | 3.2.1.3 | A. niger | α-1,4 and α-1,6-links are cleaved, from the non-reducing ends, to give β-glucose |
| Pullulanase | 3.2.1.41 | B. acidopullulyticus | Only α-1,6-links are cleaved to give straight-chain maltodextrins |

The nomenclature of the enzymes used commercially for starch hydrolysis is not particularly exacting because the EC numbers sometimes lump together enzymes with subtly different activities. For example, α-amylase may be sub classified as a liquefying or saccharifying amylase but even this classification is inadequate to encompass all the enzymes that are used in commercial starch hydrolysis. One reason for the confusion in the nomenclature is the use of the anomeric form of the released reducing group in the product rather than that of the bond being hydrolyzed; the products of bacterial and fungal α-amylases are in the α-configuration and the products of β-amylases are in the β-configuration, although all these enzymes cleave between α-1,4-linked D-(+)-glucose residues.

The α-amylases (1,4-α-D-glucan glucanohydrolases) are endohydrolases which cleave 1,4-α-D-(+)-glucosidic bonds and can bypass but cannot hydrolyze 1,6-α-D-(+)-glucosidic branch points. Commercial enzymes used for the industrial hydrolysis of starch are produced by *Bacillus amyloliquefaciens* (supplied by various manufacturers) and by *B. licheniformis* (supplied by Novo Industri A/S as Termamyl). They differ principally in their tolerance of high temperatures, Termamyl retaining more activity at up to 110° C., in the presence of starch, than the *B. amyloliquefaciens* α-amylase. The maximum Dextrose Equivalence (DE) obtainable using bacterial α-amylases is around 40 but prolonged treatment leads to the formation of maltulose (4-α-D-(+)-glucopyranosyl-D-fructose), which is resistant to hydrolysis by glucoamylase and α-amylases. Dextrose Equivalence (DE) values of 8-12 is used in most commercial processes where further saccharification is to occur. The principal requirement for liquefaction to this extent is to reduce the viscosity of the gelatinized starch to ease subsequent processing.

Various manufacturers use different approaches to starch liquefaction using α-amylases but the principles are the same. Granular starch is slurried at 30-40% (w/w) with cold water, at pH 6.0-6.5, containing 20-80 ppm $Ca^{2+}$ (which stabilizes and activates the enzyme) and the enzyme is added (via a metering pump). The α-amylase is usually supplied at high activities so that the enzyme dose is 0.5-0.6 kg tonne-1 (about 1500 U kg-1 dry matter) of starch. When Termamyl is used, the slurry of starch plus enzyme is pumped continuously through a jet cooker, which is heated to 105° C. using live steam. Gelatinization occurs very rapidly and the enzymatic activity, combined with the significant shear forces, begins the hydrolysis. The residence time in the jet cooker is very brief. The partly gelatinized starch is passed into a series of holding tubes maintained at 100-105° C. and held for 5 minute to complete the gelatinization process. Hydrolysis to the required Dextrose Equivalence (DE) is completed in holding tanks at 90-100° C. for 1 to 2 hour. These tanks contain baffles to discourage back mixing. Similar processes may be used with *B. amyloliquefaciens* α-amylase but the maximum temperature of 95° C. must not be exceeded. This has the drawback that a final 'cooking' stage must be introduced when the required Dextrose Equivalence (DE) has been attained in order to gelatinize the recalcitrant starch grains present in some types of starch which would otherwise cause cloudiness in solutions of the final product.

The liquefied starch is usually saccharified but comparatively small amounts are spray-dried for sale as 'maltodextrins' to the food industry mainly for use as bulking agents and in baby food. In this case, residual enzymatic activity may be destroyed by lowering the pH towards the end of the heating period.

Fungal α-amylase also finds use in the baking industry. It often needs to be added to bread-making flours to promote adequate gas production and starch modification during fermentation. This has become necessary since the introduction of combine harvesters. They reduce the time between cutting and threshing of the wheat, which previously was sufficient to allow a limited sprouting so increasing the amounts of endogenous enzymes. The fungal enzymes are used rather than those from bacteria as their action is easier to control due to their relative heat lability or denaturing rapidly during baking.

Hydrolyzed starch materials as described above are readily available on commercial order. It is particularly preferred to utilize maltodextrins that are commonly used as carriers and binders for tablets and granulations, film formers for encapsulation, and coating. Various grades of maltodextrin with different chemical and physical properties are available and marketed by many grain producing companies. Grain Processing Corporation of Muscatine, Iowa markets and sells various grades of maltodextrin under the trade names MALTRIN® some of which are shown in the Table 2. MALTRIN® Maltodextrins are defined by the FDA as products having Dextrose Equivalence (DE) less than 20. They are generally recognized as safe (GRAS) food ingredients. For example, MALTRIN®M040 Maltodextrin is a 5 DE, has at least 96% pentasaccharides [5 D-(+)-glucose units] bland, white, powdered carbohydrates. A solution of MALTRIN®M040 is characterized by a bland flavor and has excellent film-forming characteristics and exhibits Newtonian viscosity. At 20% to 40% levels, MALTRIN®M040 contributes more to solution viscosity than the higher Dextrose Equivalence (DE) products at comparable concentration. The Dextrose Equivalence (DE) of the hydrolyzed starch to be used in the present invention is at least 2, preferably about 3 to about 27. Aqueous film coatings are preferred due to hazards and environmental concerns involved with solvent film coating.

The MALTRIN® maltodextrins are water soluble glucose polymers which act as film formers in aqueous film coating. Any of the MALTRIN® maltodextrins may be used for film coating, however, MALTRIN®M040, M440, M100, M180, M510, QD®M440 (quickly dispersible) QD®M500 (quickly dispersible), QD®M550 (quickly dispersible), QD® M580 (quickly dispersible), QD® M600 (quickly dispersible) are preferred. They are all excellent film formers, but M040 provides a higher viscosity and a heavier film. MALTRIN® M040 may be dissolved at levels up to 40% in water. MALTRIN®M100 maltodextrin is a 10 DE, bland, white carbohydrate powder, is readily dispersible and readily soluble, has at least 88% pentasacharides. INSTANT PURE-COTE® modified starches NF are pharmaceutical grade starches that have been specially modified to produce clear, flexible films and are suitable also for this invention to provide persistent, continuous, uniform barrier films. INSTANT PURE-COTE® B793 is a pregelatinized modified corn starch NF is also marketed by Grain Processing Corporation is also suitable for this application. INSTANT PURE-COTE®B793 is a cold water-soluble modified starch that has low viscosity in solution and when used as described herein dries to a clear, persistent, continuous, uniform flexible film. Finished films and coatings are water soluble, clear and have excellent sheen. Suitable polysaccharides from other sources include, for example, the Clintose® materials from Archer Daniels Midland Company (ADM) of Decatur, Ill. including those specified as the Clintosee Maltodextrin CR5, CR10, CR15, CR18 and CR24 materials. Table 2 summarizes the chemical and physical properties of MALTRIN® materials, as published by the Grain Processing Corporation.

TABLE 2

Different Varieties of Maltodextrin (MALTRIN ®) and Chemical & Physical Properties

| Maltodextrin Grades Properties | M040 | M050 | M100 M510 | M150 | M180 | M440 | M500 | M550 | M580 | M700 | M200 | M250 | M600 |
|---|---|---|---|---|---|---|---|---|---|---|---|---|---|
| Dextrose Equivalence (DE) | 4-7 | 4-7 | 9-12 | 13-17 | 16.5-19.5 | 4-7 | 9-12 | 13-17 | 16.5-19.5 | 9-12 | 20-23 | 23-27 | 20-23 |
| pH (20% Solution) | 4.0-5.0 | 4.0-5.0 | 4.0-4.7 | 4.0-4.7 | 4.0-4.7 | 4.0-5.1 | 4.0-5.1 | 4.0-5.1 | 4.0-5.1 | 6.0-7.0 | 4.0-4.7 | 4.5-5.5 | 4.0-5.1 |
| Bulk Density | | | | | | | | | | | | | |
| lb/ft$^3$ | 32 | 34 | 34 | 35 | 38 | 19 | 21 | 22 | 25 | 8 | 38 | 39 | 25 |
| gm/cc | 0.51 | 0.54 | 0.54 | 0.57 | 0.61 | 0.30 | 0.34 | 0.35 | 0.40 | 0.13 | 0.61 | 0.63 | 0.40 |
| Solutions Characteristics* | Clear 15% Solids | Opaque | Clear 30% Solids | Clear 60% Solids | Clear 70% Solids | Clear 15% Solids | Clear 30% Solids | Clear 60% Solids | Clear 70% Solids | Clear 30% Solids | Clear 70% Solids | Clear 60% Solids | Clear 70% Solids |

*Solution clarity was determined by adding Maltrin ® Products to 82° C. water with agitation and allowing to cool to room temperature. The solution characteristics state the highest approximate concentration reached that would maintain an observed clear solution after 24 hours at room temperature.

The disclosed composition may be used in conjunction with other additives. Examples of suitable additives include a buffering agent or a pH adjusting agent, an emollient, a preservative, a moisturizing agent, a skin conditioning agent, a surfactant or wetting agent, a viscosity control agent, a colorant, an opacifying agent, or any combinations thereof.

In addition to prophylactic effects, the disclosed composition may also be used for wound healing. The composition may result in faster and qualitatively improve healing of wounds by decreasing the number of microorganisms in the vicinity of the wound.

Methods of preparing the mixture according to the disclosed composition may involve dissolving a desired amount of viscosity control agent, such as xanthan gum, and, optionally, any desired additives in the solvent. The solution is then mixed, for example, in a mixer until it is homogeneous and no lumps are visible. Liquid sorbitol and/or glycerin are then pumped in and mix until the solution becomes homogeneous. Polysaccharide derivatives, such as maltodextrin are then added by dispensing slowly to the vortex and mix until they completely dissolve. Antimicrobial agents, such as salicylic acid, are added slowly to the vortex and mix until they completely dissolve. The pH is adjusted using acids or bases or buffering agents if necessary. Finally, coloring agent is added if desired.

Useful concentrations are those where the percentage of each functional ingredient or mixture of ingredients including antimicrobial agents by total weight of the composition is preferably from about 0.02% to 30% by weight for each ingredient and 50% to 95% for the solvent; more preferably from about 0.03% to 25% for each ingredient and from about 60% to 95% for the solvent; most preferably from about 0.1% to 20% for the antimicrobial agent, from about 0.1% to 20% for the barrier film-forming agent, from about 0.1% to 10% for the thickening agent, from about 0.1% to about 25% for emollients or moisturizing agents, from about 0.1% to about 10% for skin conditioning agents, and from about 65% to 85% for the solvent.

As used herein, the term "subject" shall include, for example, a domestic livestock species, a laboratory animal species, a zoo animal, a companion animal or a human. In a particular embodiment, "subject" refers more specifically to dairy animals; preferably, the subject is a cow.

The term "additive" shall mean any component that is not an antimicrobial agent or a pharmaceutical carrier. A pharmaceutical carrier is generally a bulk solvent used to dilute or solubilize the components of the composition.

The term "substantially free" means that the component is virtually absent from a composition. As would occur in any chemical preparation processes, small amount of contaminants may exist in the composition, but "substantially free" shall mean that the final product contains less than 1% of the specified ingredient.

The term "apply" or "applied" shall be interpreted broadly. Thus, the composition may be caused to be in contact with the skin of the animal by a variety of means. Such means include but are not limited to spraying, paint brushing, spreading, foaming, and teat-dipping and other ways that are found acceptable in the dairy industry.

Antimicrobial Agents

The preferred composition includes from 0.1% to 20% by weight of at least one antimicrobial active agent. Throughout this disclosure, the terms "antimicrobial," "biocidal" and "germicidal" are used interchangeably. All these terms are used to describe an effect of certain chemicals, when used alone or in combination, accelerate the demise or limit the growth of viable microorganisms. The term microorganism, as used in this disclosure, refers to the same organisms that are commonly known as microorganisms in the field of microbiology. Examples of microorganisms include but are not limited to bacteria, fungi, viruses and the like.

Various antimicrobial agents may be used in the disclosed composition. Examples of such antimicrobial agents include an organic acid with benzyl alcohol and/or a low molecular weight aliphatic alcohol having a carbon number less than five. In particular, lactic acid, salicylic acid, benzyl alcohol, and/or isopropyl alcohol may suffice to make effective biocidal compositions.

Traditional antimicrobial agents are the components of a composition that destroy microorganisms or prevent or inhibit their replication. In one aspect, the combined antimicrobial agents discussed above may be used to replace or eliminate the need for traditional antimicrobial agents in a wide variety of applications. In another aspect, antimicrobial compositions according to the disclosed embodiments below may be used in combination with these traditional antimicrobial agents, for example, to achieve an effective kill at lower concentrations of traditional antimicrobial agents.

Conventional antimicrobial agents may also be used in addition to the previously described antimicrobial agents. These conventional antimicrobial agents for use in teat dip applications include iodophors, quaternary ammonium compounds, hypochlorite releasing compounds (e.g. alkali hypochlorite, hypochlorous acid), oxidizing compounds (e.g.

organic peroxide, hydrogen peroxide, peroxyacids; hypochlorite, chlorine dioxide, hypochlorous acid), protonated carboxylic acids (e.g. heptanoic, octanoic, nonanoic, decanoic, undecanoic acids), acid anionics (e.g. alkylaryl sulfonic acids, alkyl sulfonic acids, aryl sulfonic acids), chlorine dioxide from alkali chlorite by an acid activator, and bisbiguamides such as chlorohexidine. Phenolic antibacterial agents may be chosen from 2,4,4'-trichloro-2'-hydroxydiphenylether, which is known commercially as Triclosan and may be purchased from Ciba Specialty Chemicals as IRGASAN™ and IRGASAN DP 300™) having the following structural Formula (VII):

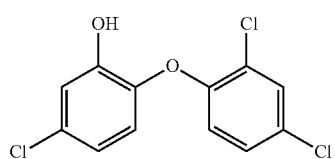

(VIII)

Another such antibacterial agent is 4-chloro-3,5-dimethyl phenol (p-chloro-m-xylenol), which is also known as PCMX and is commercially available as NIPACIDE PX and NIPACIDE PX-P having the following structural Formula (IX):

(IX):

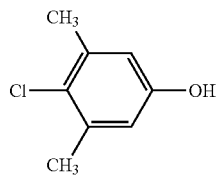

Other traditional germicides include formaldehyde releasing compounds such as glutaraldehyde, 2-bromo-2-nitro-1,3-propanediol (bronopol) having the following structural Formula (X).

Formula (X):

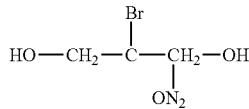

Viscosity Control Agents

Solution viscosity may be thinned by the addition of alcohol or water; however, the teat dip compositions generally benefit from the use of a thickening agent in an amount generally ranging from 0.1% to about 10% by weight of the composition. The particular amount of thickening agent is less important than its effect to adjust viscosity into a desired range. Viscosity control agents may be added to formulate the antimicrobial applications according to an intended environment of use. In one example, it is advantageous for some formulations to have an optimized solution viscosity to impart vertical clinging of the product onto a teat. This type of viscous product, especially one having a suitable thixotropic, pseudoplastic or viscoelastic gel strength, minimizes dripping of the product to avoid wastage and is particularly advantageous in teat dip formulations. Teat dip formulations may benefit from a preferred dynamic viscosity ranging from 50-4000 cPs, 100 cPs to 3000 cPs measured by a Brookfield viscometer, model LV, measured in cPs unit at ambient temperature (25° C.) with a spindle #2@30 rpm.

Suitable thickeners or viscosity control agents include plant gum materials, for example guar gum; starch and starch derivatives, for example hydroxyethyl starch or cross-linked starch; microbial polysaccharides, for example xanthan gum, sea weed polysaccharides, for example sodium alginate, carrageenan, curdlan, pullulan or dextran, dextran sulfate, whey, gelatin, chitosan, chitosan derivatives, polysulfonic acids and their salts, polyacrylamide, and glycerol. Cellulosic thickeners may be used including hemicellulose, for example arabinoxylanes and glucomannanes; cellulose and derivatives thereof, for example methyl cellulose, ethyl cellulose, hydroxyethyl cellulose or carboxymethyl cellulose. The cellulosic thickeners form part of the total amount of polysaccharide material and are preferably used in amounts that do not exceed the preferably do not exceed the majority component of polysaccharide material having the DE value ranging from 2 to 50 as described above.

pH Adjusting Agents

The pH value of the composition may be adjusted by the addition of acidic or basic or buffering materials. Generally, an acidic pH is preferred for teat dip products. Suitable acids for use as pH adjusting agents may include, for example, citric acid, lactic acid, phosphoric, phosphorous, sulfamic, nitric, and hydrochloric acids. Mineral acids may be used to drastically lower the pH. The pH may be raised or made more alkaline by addition of an alkaline agent such as sodium hydroxide, ammonium hydroxide, potassium hydroxide, sodium carbonate, or sodium bicarbonate or combinations thereof.

The preferred pH range of the composition is from 1.5 to 10, 2.0 to 9.0 for use in teat dip formulations and other applications that necessitate contact with the skin. More preferably, the pH is from 2 to 9.0 for a teat dip formulation. Traditional acid buffering agents such as citric acid, lactic acid, phosphoric acid may also be used to maintain the pH buffer.

Wetting Agents and Surfactants

Wetting agents or surfactants may be included to formulate the disclosed compositions for an intended environment of use. Typical wetting agents or surfactants are used to wet the surface of application, reduce surface tension of the surface of application so that the product can penetrate easily on the surface and remove unwanted soil. The wetting agents or surfactants of the formulation increase overall detergency of the formula, solubilize or emulsify some of the organic ingredients that otherwise would not dissolve or emulsify, and facilitate penetration of active ingredients deep onto the surface of the intended application surfaces, such as animal teats.

Suitably effective surfactants may include anionic, cationic, nonionic, zwitterionic and amphoteric surfactants. Wetting agents and surfactants used in the inventive applications can be high foaming, low foaming and non foaming type. Suitable anionic surfactants can be chosen from alkyl sulfonic acid, alkyl sulfonate salt, linear alkylbenzene sulfonic acid, a linear alkylbenzene sulfonate, an alkyl α-sulfomethyl ester, an α-olefin sulfonate, an alcohol ether sulfate, an alkyl sulfate, an alkylsulfo succinate, a dialkylsulfo succinate, and their alkali metal, alkaline earth metal, amine and ammonium salts thereof. Specific examples are linear $C_{10}$-$C_{16}$ alkylbenzene sulfonic acid, linear $C_{10}$-$C_{16}$ alkylbenzene sulfonate or alkali metal, alkaline earth metal, amine and ammonium salt thereof e.g. sodium dodecylbenzene sulfonate, sodium $C_{14}$-$C_{16}$ α-olefin sulfonate, $C_{12}$-$C_{18}$, sodium methyl α-sulfomethyl ester and $C_{12}$-$C_{18}$, disodium methyl α-sulfo fatty acid salt. Suitable nonionic surfactants can be chosen from alkyl polyglucoside, alkyl ethoxylated alcohol, alkyl propoxylated alcohol, ethoxylatedpropoxylated alcohol, sorbitan, sorbitan ester, alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

Opacifying Agents and Dyes

An opacifying agent or dye may be included in the composition. Color on the dairy animal teats may serve as an indicator that a particular cow has been treated. To preclude any problems with possible contamination of milk, only FD&C Certified (food grade) dyes should be used. There are many FD&C dyes available and suitable which are FD&C Red #40, FD&C Yellow #6, FD&C Yellow #5, FD&C Green #3 and FD&C Blue #1 and combinations thereof. D&C Orange #4 can also be used either alone or in mixture thereof. Titanium dioxide ($TiO_2$) is widely used as an opacifier and can also be used in combination with various colorants.

Preservatives

Some known teat dips and hand sanitizers include ethylenediaminetetraacetic acid (EDTA) and its alkali salts which act as a chelating agent to remove metal ions from hard water. The metal ions, if not removed from the composition, facilitate the metalloenzyme reactions that produce energy for bacterial cell replication. Other traditional preservatives, for example, paraban, methyl paraban, ethyl paraban, glutaraldehyde, may also be used.

Solvents

The preferred solvent for the present composition is water. However, one skilled in the art will recognize that solvents or compatible materials other than water may be used to serve the same purpose. In some embodiments, a composition may contain at least about 70% water and preferably at least about 75% water by weight based on the total weight of the formulation. Propylene glycol, ethylene glycol can also be used as a solvent either alone or in combination with water. Short chain alcohols having a carbon number less than six may be used as solvents or co solvents to enhance speed of drying as the composition forms a film.

EXAMPLES

The compositions and methods will be further illustrated by the following non-limiting examples.

Representative Formulations (Examples DL-1 to DL-49)

The composition of the present disclosure may be prepared according to the following steps. The order of addition is intended to be a guideline only, and may be modified by a person of ordinary skills in the art. The total amount of the mixture can also be adjusted according to the intended application. The amount of each component to be added is set forth in examples identified as formulation DL-1 to DL-49 in Tables 3-8.

Unless otherwise specified, ingredient amounts reported in these tables are on the basis of weight percent to the total composition. It will be appreciated that the overall stability of these mixtures was quite good; however, especially as shown in Table 7, some of the mixtures developed a haziness or precipitate (PPT). The primary cause of this was precipitation of salicylic acid, as confirmed by infrared and HPLC analysis. It will be appreciated that increased amounts of lactic acid defined as a ratio of lactic acid to salicylic acid exceeding 2:1 (w/w) may facilitate long term solubility of lactic acid, as may the inclusion of sodium hydroxide in a ratio exceeding 2:3. Repeat numbers for germicidal efficacy indicate multiple such tests of the same mixture. Variances in repeat runs of germicidal efficacy are primarily due to separation of the mixture, where it will be further appreciated that differences on the order of on half log are to be expected from these kinds of tests. Film quality was tested using different amounts of the compositions, as shown in the Tables.

Comparative Film Evaluation

The quality of continuous, uniform film, persistency barrier of the teat dip was evaluated by a method described as below.

Materials used were 400 mL of product to be evaluated, stainless steel panels (6×3 inches), and 600 mL beakers. The panels were washed, dried and weighted on analytical balance. Each panel had a line drawn at 2 inches high from the bottom. The panels were dipped in product to the marked line and then they were hung to dry for four hours. After four hours they were weighted again and the amount of dry teat dip that retained on the panel was calculated as the difference between the weight after four hours and the initial weight. The film, barrier quality was evaluated based on 1 to 5 scales. The numerical rating was as follows:

1. not dry on the whole surface, stainless steel is partially visible (the worst)
2. tacky film, not continuous or disuniform continuity
3. tacky film, some discontinuity
4. dry continuous uniform film (ideal teat dip film for long term persistency and easy removal)
5. completely dry, not tacky, continuous, and uniform film (the best).

After the film general appearance and weight were evaluated, the film solubility was tested. The panels were let to stand in 150 mL of cold tap water and the timer was set. The time until the film was dissolved was recorded. If the film was completely dissolved without mixing, it was the most desired and appreciated. Films that need longer time to dissolve were better than films that dissolved in less than 1 minute in terms of persistency. All comparative products were evaluated simultaneously. On the whole, the films superior films in comparison to existing commercial products. Tables 3-4 show the comparison results.

Product formulations physical stability was evaluated by aging the samples at −15° C., 4° C., 25° C., 40° C., 45° C. and 50° C. for extended period of time typically more than six months. Samples are periodically checked visually for precipitation, separation, coagulation, crystallization etc. and by freeze-thaw cycles for samples aged at cold temperature. Product is considered physically stable if none of the physical attributes described above is observed or present. The germicide active ingredients are also analyzed for their chemical stability, germicidal efficacy as well as their pH, viscosity etc. The product is considered chemically and germicidically stable, if the concentrations of the active ingredients remain within ±5% of the initial concentration at the time of manufacture.

The product germicidal efficacy was also tested by the standard germicidal efficacy test on samples that are aged for extended period at elevated temperature (for example at 50° C.) to simulate the life time of the product. The germicidal efficacy of the formulations was evaluated by the standard AOAC official method 960.09 for germicidal and detergent sanitizing action of disinfectants, European Standard test methods EN 1040 for chemical disinfectants and antiseptics-basic bactericidal activity and EN 1656 for quantitative suspension test for the evaluation of bacterial activity of chemical disinfectants and antiseptics used in veterinary field. Bacterial growth inhibition test was done by applying the germicidal product on a Petri dish and allowed to dry for 4 hours. Bacteria and agar and media were added on the top of the dried product and let the bacteria grow for 24 hours and measure the bacteria count.

TABLE 3

Barrier Film-forming Teat Dip Compositions: Persistent Barrier Film Evaluation

| Maltodexrin Film Improvement Barrier/ Film Optimization with Maltodextrin Ingredients | DL-1 Concn, % | DL-2 Concn, % | DL-3 Concn, % | DL-4 Concn, % | DL-5 Concn, % | DL-6 Concn, % | DL-7 Concn, % | DL-8 Concn, % | DL-9 Concn, % | DL-10 Concn, % |
|---|---|---|---|---|---|---|---|---|---|---|
| Water | 75.56 | 75.06 | 74.56 | 74.06 | 75.46 | 75.21 | 74.96 | 74.46 | 73.16 | 71.26 |
| Keltrol R-Regular[1] | 0.40 | 0.40 | 0.40 | 0.40 | 0.40 | 0.40 | 0.40 | 0.40 | 0.40 | 0.40 |
| Polyvinylpyrrolidone K-30 | 0.70 | 0.70 | 0.70 | 0.70 | 0.80 | 0.80 | 0.80 | 0.80 | 0.60 | 0.50 |
| Salicylic Acid USP | 0.90 | 0.90 | 0.90 | 0.90 | 0.90 | 0.90 | 0.90 | 0.90 | 0.90 | 0.90 |
| Sorbitol 70% USP | 14.29 | 14.29 | 14.29 | 14.29 | 14.29 | 14.29 | 14.29 | 14.29 | 14.29 | 14.29 |
| Allantoin | 0.10 | 0.10 | 0.10 | 0.10 | 0.10 | 0.10 | 0.10 | 0.10 | 0.10 | 0.10 |
| Maltodextrin M040[2] | 0.50 | 1.00 | 1.50 | 2.00 | 0.50 | 0.75 | 1.00 | 1.50 | 3.00 | 5.00 |
| L(+)-Lactic Acid (88%) USP-ADM | 4.00 | 4.00 | 4.00 | 4.00 | 4.00 | 4.00 | 4.00 | 4.00 | 4.00 | 4.00 |
| Benzyl Alcohol | 1.00 | 1.00 | 1.00 | 1.00 | 1.00 | 1.00 | 1.00 | 1.00 | 1.00 | 1.00 |
| Pluronic F108[3] | 0.50 | 0.50 | 0.50 | 0.50 | 0.50 | 0.50 | 0.50 | 0.50 | 0.50 | 0.50 |
| Sodium Dioctylsulfosuccinate (75%) | 0.15 | 0.15 | 0.15 | 0.15 | 0.15 | 0.15 | 0.15 | 0.15 | 0.15 | 0.15 |
| Tween 80[4] | 0.40 | 0.40 | 0.40 | 0.40 | 0.40 | 0.40 | 0.40 | 0.40 | 0.40 | 0.40 |
| Sodium Hydroxide (50%) | 1.50 | 1.50 | 1.50 | 1.50 | 1.50 | 1.50 | 1.50 | 1.50 | 1.50 | 1.50 |
| FD&C Yellow # 5 | 0.030 | 0.030 | 0.030 | 0.030 | 0.030 | 0.030 | 0.030 | 0.030 | 0.030 | 0.030 |
| FD&C Blue #1 | 0.020 | 0.020 | 0.020 | 0.020 | 0.020 | 0.020 | 0.020 | 0.020 | 0.020 | 0.020 |
|  | 100 | 100 | 100 | 100 | 100 | 100 | 100 | 100 | 100 | 100 |
| Specific Gravity, gm/mL | 1.075 | 1.075 | 1.075 | 1.075 | 1.075 | 1.075 | 1.075 | 1.075 | 1.075 | 1.075 |
| Brookfield Viscosity LV2 30 rpm; cPs | 539 | 535 | 544 | 560 | 489 | 567 | 548 | 586 | 469 | 651 |
| pH, Neat | 3.50 | 3.50 | 3.50 | 3.50 | 3.50 | 3.50 | 3.50 | 3.50 | 3.50 | 3.50 |
| Product Retention (Adherence) Amount of Product Adhered, gm: |  |  |  |  |  |  |  |  |  |  |
| Test Tube/SS Panel | .100/.208 | .057/.174 | .067/.188 | .088/.211 | .88/.186 | .065/.188 | .107/.243 | .074/.220 | .109/.210 | .117/.294 |
| Film Quality (1-5, 5 being best) |  |  |  |  |  |  |  |  |  |  |
| Test Tube/SS Panel | 4.0/3.0 | 4.0/4.0 | 4.0/4.0 | 4.0/4.0 | 4.0/4.0 | 4.0/4.0 | 4.0/3.0 | 4.0/4.0 | 4.0/4.0 | 4.0/4.0 |

[1]Keltrol R is a xanthan gum obtained from Kelco Company
[2]Maltodextrin M040 is a hydrolyzed starch obtained from Grain Processing Corporation
[3]Pluronic F-108, is an ethoxylated/propoxylated block copolymer of propylene glycol obtained from BASF
[4]Tween 80 is a polyoxyethylene sorbitan ester of oleic acid obtained from Uniqema

TABLE 4

Barrier Film-forming Teat Dip Compositions: Persistent Barrier Film Evaluation

| Maltodexrin Film Improvement Barrier/Fim Optimization with Maltodextrin Ingredients | DL-11 Wt, % | DL-12 Wt, % | DL-13 Wt, % | DL-14 Wt, % | DL-15 Wt, % | DL-16 Wt, % |
|---|---|---|---|---|---|---|
| Water | 78.17 | 77.27 | 76.37 | 75.47 | 74.57 | 73.67 |
| Keltrol R-Regular[1] | 0.40 | 0.40 | 0.40 | 0.40 | 0.40 | 0.40 |
| Polyvinylpyrrolidone K-30 | 0.80 | 0.70 | 0.60 | 0.50 | 0.40 | 0.30 |
| Salicylic Acid USP | 0.90 | 0.90 | 0.90 | 0.90 | 0.90 | 0.90 |
| Sorbitol 70% USP | 11.43 | 11.43 | 11.43 | 11.43 | 11.43 | 11.43 |
| Allantoin | 0.10 | 0.10 | 0.10 | 0.10 | 0.10 | 0.10 |
| Maltodextrin M040[2] | 1.00 | 2.00 | 3.00 | 4.00 | 5.00 | 6.00 |
| L(+)-Lactic Acid (88%) USP-ADM | 4.00 | 4.00 | 4.00 | 4.00 | 4.00 | 4.00 |
| Benzyl Alcohol | 1.00 | 1.00 | 1.00 | 1.00 | 1.00 | 1.00 |
| Pluronic F108[3] | 0.20 | 0.20 | 0.20 | 0.20 | 0.20 | 0.20 |
| Sodium Dioctylsulfosuccinate (75%) | 0.15 | 0.15 | 0.15 | 0.15 | 0.15 | 0.15 |

TABLE 4-continued

Barrier Film-forming Teat Dip Compositions: Persistent Barrier Film Evaluation

| | | | | | | |
|---|---|---|---|---|---|---|
| Tween 80[4] | 0.30 | 0.30 | 0.30 | 0.30 | 0.30 | 0.30 |
| Sodium Hydroxide (50%) | 1.50 | 1.50 | 1.50 | 1.50 | 1.50 | 1.50 |
| FD&C Yellow # 5 | 0.030 | 0.030 | 0.030 | 0.030 | 0.030 | 0.030 |
| FD&C Blue #1 | 0.020 | 0.020 | 0.020 | 0.020 | 0.020 | 0.020 |
| | 100 | 100 | 100 | 100 | 100 | 100 |
| Specific Gravity, gm/mL | 1.075 | 1.075 | 1.075 | 1.075 | 1.075 | 1.075 |
| Brookfield Viscosity LV2 30 rpm; cPs | 635 | 655 | 652 | 665 | 671 | 643 |
| pH, Neat | 3.49 | 3.53 | 3.48 | 3.44 | 3.51 | 3.49 |
| Product Retention (Adherence) Amount of Product Adhered, gm: | | | | | | |
| Test Tube/SS Panel | .036/.118 | .050/.114 | .052/.134 | .054/.116 | .120/.192 | .119/.304 |
| Film Quality (1-5, 5 being best) | | | | | | |
| Test Tube/SS Panel | 3.0/4.0 | 4.0/4.0 | 4.0/3.5 | 4.0/3.0 | 4.0/3.0 | 4.0/4.0 |

Maltodexrin Film Improvement
Barrier/Fim Optimization with Maltodextrin

| Ingredients | DL-17 Wt, % | DL-18 Wt, % | DI-19 Wt, % | DL-20 Wt, % | DL-21 Wt, % | DL-22 Wt, % |
|---|---|---|---|---|---|---|
| Water | 71.11 | 70.11 | 72.67 | 72.57 | 73.57 | 71.21 |
| Keltrol R-Regular[1] | 0.40 | 0.40 | 0.40 | 0.40 | 0.40 | 0.40 |
| Polyvinylpyrrolidone K-30 | 0.00 | 0.00 | 0.30 | 0.40 | 0.40 | 0.50 |
| Salicylic Acid USP | 0.90 | 0.90 | 0.90 | 0.90 | 0.90 | 0.90 |
| Sorbitol 70% USP | 14.29 | 14.29 | 11.43 | 11.43 | 11.43 | 14.29 |
| Allantoin | 0.10 | 0.10 | 0.10 | 0.10 | 0.10 | 0.10 |
| Maltodextrin M040[2] | 6.00 | 7.00 | 7.00 | 7.00 | 6.00 | 5.00 |
| L(+)-Lactic Acid (88%) USP-ADM | 4.00 | 4.00 | 4.00 | 4.00 | 4.00 | 4.00 |
| Benzyl Alcohol | 1.00 | 1.00 | 1.00 | 1.00 | 1.00 | 1.00 |
| Pluronic F108[3] | 0.20 | 0.20 | 0.20 | 0.20 | 0.20 | 0.50 |
| Sodium Dioctylsulfosuccinate (75%) | 0.15 | 0.15 | 0.15 | 0.15 | 0.15 | 0.15 |
| Tween 80[4] | 0.30 | 0.30 | 0.30 | 0.30 | 0.30 | 0.40 |
| Sodium Hydroxide (50%) | 1.50 | 1.50 | 1.50 | 1.50 | 1.50 | 1.50 |
| FD&C Yellow # 5 | 0.030 | 0.030 | 0.030 | 0.030 | 0.030 | 0.030 |
| FD&C Blue #1 | 0.020 | 0.020 | 0.020 | 0.020 | 0.020 | 0.020 |
| | 100 | 100 | 100 | 100 | 100 | 100 |
| Specific Gravity, gm/mL | 1.075 | 1.075 | 1.075 | 1.075 | 1.075 | 1.075 |
| Brookfield Viscosity LV2 30 rpm; cPs | 643 | 643 | 653 | 655 | 687 | 651 |
| pH, Neat | 3.49 | 3.49 | 3.49 | 3.53 | 3.49 | 3.50 |
| Product Retention (Adherence) Amount of Product Adhered, gm: | | | | | | |
| Test Tube/SS Panel | .119/.304 | .119/.304 | .114/.256 | .230/.277 | .106/.247 | |
| Film Quality (1-5, 5 being best) | | | | | | |
| Test Tube/SS Panel | 4.0/4.0 | 4.0/4.0 | 4.0/3.0 | 4.0/4.0 | 4.0/3.0 | 4.0/4.0 |

[1]Keltrol R is a xanthan gum obtained from Kelco Company
[2]Maltodextrin M040 is a hydrolyzed starch obtained from Grain Processing Corporation
[3]Pluronic F-108, is an ethoxylated/propoxylated block copolymer of propylene glycol obtained from BASF
[4]Tween 80 is a polyoxyethylene sorbitan ester of oleic acid obtained from Uniqema

TABLE 5

Barrier Film-forming Teat Dip Compositions: Persistent Barrier Film and Germicidal Efficacy Evaluation

| GERMICIDAL EFFICACY Ingredients | DL-23 Wt % | DL-24 Wt % | DL-25 Wt % | DL-26 Wt % | DL-27 Wt % | DL-28 Wt % | DL-29 Wt % | DL-30 Wt % | DL-31 Wt % |
|---|---|---|---|---|---|---|---|---|---|
| Water | 72.11 | 73.61 | 73.61 | 73.61 | 73.61 | 73.61 | 73.66 | 73.71 | 73.81 |
| Keltrol R[1] | 0.40 | 0.40 | 0.40 | 0.40 | 0.40 | 0.40 | 0.40 | 0.40 | 0.40 |
| Sorbitol 70% | 14.29 | 14.29 | 14.29 | 14.29 | 14.29 | 14.29 | 14.29 | 14.29 | 14.29 |
| Maltrin M040[2] | 5.00 | 5.00 | 5.00 | 5.00 | 5.00 | 5.00 | 5.00 | 5.00 | 5.00 |
| Salicylic Acid | 0.90 | 0.90 | 0.90 | 0.90 | 0.90 | 0.90 | 0.85 | 0.80 | 0.70 |
| Allantoin | 0.10 | 0.10 | 0.10 | 0.10 | 0.10 | 0.10 | 0.10 | 0.10 | 0.10 |
| Lactic Acid (88%) USP | 4.00 | 4.00 | 4.00 | 4.00 | 4.00 | 4.00 | 4.00 | 4.00 | 4.00 |
| Benzyl Alcohol | 1.00 | 1.00 | 1.00 | 1.00 | 1.00 | 1.00 | 1.00 | 1.00 | 1.00 |
| Pluronic F108[3] | 0.20 | 0.20 | 0.20 | 0.20 | 0.20 | 0.20 | 0.20 | 0.20 | 0.20 |
| Sodium Dioctylsulfosuccinate (75%) | 0.15 | 0.15 | 0.15 | 0.15 | 0.15 | 0.15 | 0.15 | 0.15 | 0.15 |
| Tween 80[4] | 0.30 | 0.30 | 0.30 | 0.30 | 0.30 | 0.30 | 0.30 | 0.30 | 0.30 |

TABLE 5-continued

Barrier Film-forming Teat Dip Compositions: Persistent Barrier Film and Germicidal Efficacy Evaluation

| GERMICIDAL EFFICACY Ingredients | DL-23 Wt % | DL-24 Wt % | DL-25 Wt % | DL-26 Wt % | DL-27 Wt % | DL-28 Wt % | DL-29 Wt % | DL-30 Wt % | DL-31 Wt % |
|---|---|---|---|---|---|---|---|---|---|
| Sodium Hydroxide (50%) | 1.50 | 1.5 + QS* | 1.5 + QS* | 1.5 + QS* | 1.5 + QS* | 1.5 + QS* | 1.5 − QS* | 1.5 − QS* | 1.5 − QS* |
| FD&C Yellow 5-E102 | 0.03 | 0.03 | 0.03 | 0.03 | 0.03 | 0.03 | 0.03 | 0.03 | 0.03 |
| FD&C Blue 1-E133 | 0.02 | 0.02 | 0.02 | 0.02 | 0.02 | 0.02 | 0.02 | 0.02 | 0.02 |
| pH | 3.50 | 3.60 | 3.70 | 3.80 | 3.90 | 4.00 | 3.50 | 3.50 | 3.50 |
| Physical/Chemical Stability** | OK | OK | OK | OK | OK | OK | OK | OK | OK |
| EN 1656 Test: 25° C./30 Second Log Reduction | | | | | | | | | |
| E. Coli | 7.1 | 7.1 | 7.1 | 7.1 | 7.1 | 1.9 | 7.1 | 7.1 | 7.1 |
| Staph. Aureus | 6.9 | 6.9 | 2.6 | 3.1 | 3.6 | 3.7 | 6.9 | 6.9 | 6.9 |

*QS: Quantity of Sodium Hydroxide and Water are adjusted in the formula to obtain the required pH
**Physical & Chemical hydrability was assessed at −15° C., 4° C., 25° C., 40° C., 45° C. and 50° C.; Physical Instability is reported at precipitate (PPT), Haze and OK represents Physical and Chemical Stability under all temperatures conditions
[1]Keltrol R is a xanthan gum obtained from Kelco Company
[2]Maltodextrin M040 is a hydrolyzed starch obtained from Grain Processing Corporation
[3]Pluronic F-108, is an ethoxylated/propoxylated block copolymer of propylene glycol obtained from BASF
[4]Tween 80 is a polyoxyethylene sorbitan ester of oleic acid obtained from Uniqema

TABLE 6

Barrier Film-Forming Compositions: Persistent Barrier Film and Germicidal Efficacy Evaluation

| GERMICIDAL PROPERTY Ingredients | DL-32 Wt % | DL-33 Wt % | DL-34 Wt % | DL-35 Wt % | DL-36 Wt % |
|---|---|---|---|---|---|
| Water | 72.11 | 77.56 | 77.76 | 77.71 | 77.51 |
| Keltrol R[1] | 0.40 | 0.40 | 0.40 | 0.40 | 0.40 |
| Sorbitol 70% | 14.29 | 14.29 | 14.29 | 14.29 | 14.29 |
| Maltrin M040[2] | 5.00 | 0.00 | 0.00 | 0.00 | 0.00 |
| Polyvinyl Pyrrolodine | 0.00 | 0.80 | 0.80 | 0.80 | 0.80 |
| Salicylic Acid | 0.90 | 0.90 | 0.80 | 0.70 | 0.60 |
| Allantoin | 0.10 | 0.10 | 0.10 | 0.10 | 0.10 |
| Lactic Acid (88%) USP | 4.00 | 4.00 | 4.00 | 4.00 | 4.00 |
| Benzyl Alcohol | 1.00 | 1.00 | 1.00 | 1.00 | 1.00 |
| Pluronic F108[3] | 0.20 | 0.20 | 0.20 | 0.20 | 0.20 |
| Sodium Dioctylsulfosuccinate (75%) | 0.15 | 0.15 | 0.15 | 0.15 | 0.15 |
| Tween 80[4] | 0.30 | 0.30 | 0.30 | 0.30 | 0.30 |
| Sodium Hydroxide (50%) | 1.50 | 0.25 | 0.15 | 0.30 | 0.60 |
| FD&C Yellow 5-E102 | 0.03 | 0.03 | 0.03 | 0.03 | 0.03 |
| FD&C Blue 1-E133 | 0.02 | 0.02 | 0.02 | 0.02 | 0.02 |
| pH | 3.49 | 3.51 | 3.49 | 3.50 | 3.50 |
| Physical/Chemical Stability* | OK | OK | OK | OK | OK |
| EN 1656 Test: 25° C./30 Second Log Reduction | | | | | |
| | | | | Lower Salicylic Acid Concentration gives Lower Kill | |
| E. Coli | 7.0 | 7.0 | 7.0 | 3.1 | 7.0 |
| | 7.0 | 7.1 | 7.1 | 7.1 | 7.1 |
| Staph. Aureus | 7.1 | 6.8 | 6.8 | 6.8 | 6.8 |
| | 7.1 | 6.6 | 6.6 | 4.0 | 3.1 |

*Physical & Chemical stability was assessed at −15° C., 4° C., 25° C., 40° C., 45° C. and 50° C.; Physical Instability is reported at precipitate (PPT), Haze and OK represents Physical and Chemical Stability under all temperatures conditions
[1]Keltrol R is a xanthan gum obtained from Kelco Company
[2]Maltodextrin M040 is a hydrolyzed starch obtained from Grain Processing Corporation
[3]Pluronic F-108, is an ethoxylated/propoxylated block copolymer of propylene glycol obtained from BASF
[4]Tween 80 is a polyoxyethylene sorbitan ester of oleic acid obtained from Uniqema

TABLE 7

Barrier Film-Forming Compositions: Persistent Barrier Film and Germicidal Efficacy Evaluation

| Germicidal Efficacy Ingredients | DL-23 Wt % | DL-37 Wt % | DL-38 Wt % | DL-39 Wt % | DL-40 Wt % | DL-41 Wt % |
|---|---|---|---|---|---|---|
| Water | 72.11 | 77.36 | 76.96 | 76.31 | 75.01 | 73.36 |
| Keltrol R[1] | 0.40 | 0.40 | 0.40 | 0.40 | 0.40 | 0.40 |
| Sorbitol 70% | 14.29 | 14.29 | 14.29 | 14.29 | 14.29 | 14.29 |
| Maltrin M040[2] | 5.00 | 5.00 | 5.00 | 5.00 | 5.00 | 5.00 |
| Salicylic Acid | 0.90 | 0.90 | 0.90 | 0.90 | 0.90 | 0.90 |
| Allantoin | 0.10 | 0.10 | 0.10 | 0.10 | 0.10 | 0.10 |
| Lactic Acid (88%) USP | 4.00 | 0.00 | 0.50 | 1.00 | 2.00 | 3.00 |
| Benzyl Alcohol | 1.00 | 1.00 | 1.00 | 1.00 | 1.00 | 1.00 |
| Pluronic F108[3] | 0.20 | 0.20 | 0.20 | 0.20 | 0.20 | 0.20 |
| Sodium Dioctylsulfosuccinate (75%) | 0.15 | 0.15 | 0.15 | 0.15 | 0.15 | 0.15 |
| Tween 80[4] | 0.30 | 0.30 | 0.30 | 0.30 | 0.30 | 0.30 |
| Sodium Hydroxide (50%) | 1.50 | 0.25 | 0.15 | 0.30 | 0.60 | 1.25 |

TABLE 7-continued

Barrier Film-Forming Compositions: Persistent Barrier Film and Germicidal Efficacy Evaluation

| | | | | | | |
|---|---|---|---|---|---|---|
| FD&C Yellow 5-E102 | 0.03 | 0.03 | 0.03 | 0.03 | 0.03 | 0.03 |
| FD&C Blue 1-E133 | 0.02 | 0.02 | 0.02 | 0.02 | 0.02 | 0.02 |
| pH | 3.49 | 3.51 | 3.49 | 3.52 | 3.48 | 3.58 |
| Physical/Chemical Stability* | OK | PPT | PPT | Haze | OK | OK |

*Physical & Chemical stability was assessed at −15° C., 4° C., 25° C., 40° C., 45° C. and 50° C.; Physical Instability is reported at precipitate (PPT), Haze and OK represents Physical and Chemical Stability under all temperatures conditions

Germicidal Efficacy Data
EN 1656 Test: 25° C./30 Second: Log Reduction

| | Duplicate Runs | | | Duplicate Runs | | Duplicate Runs | | Duplicate Runs | |
|---|---|---|---|---|---|---|---|---|---|
| *E. Coli* | | | | | | | | | |
| Fresh Product | 7.0 | 7.0 | 7.0 | 7.1 | 7.1 | 7.1 | 7.1 | 7.1 | 7.1 | 7.1 |
| 70 Days Aged Product @ 50° C. | 7.0 | 7.1 | | | | | | | | |
| 70 Days Aged Product @ 50° C. | 7.0 | 7.1 | | | | | | | | |
| 38 Days Aged Product @ 50° C. | 7.0 | 7.1 | | | | | | | | |
| Scale Up Batch Sample | 7.0 | 5.3 | | | | | | | | |
| *Staph. Aureus* | | | | | | | | | |
| Fresh Product | 7.1 | 7.1 | 7.1 | 7.0 | 7.0 | 7.0 | 7.0 | 6.6 | 7.0 | 7.0 |
| 70 Days Aged sample @ 50° C. | 7.1 | 6.5 | | | | | | | | |
| 70 Days Aged sample @ 50° C. | 6.5 | 7.0 | | | | | | | | |
| 38 Days Aged sample @ 50° C. | 6.5 | 7.0 | | | | | | | | |
| Scale Up Batch Sample | 6.5 | 6.6 | | | | | | | | |

Chemical Stability of Germicidal Ingredient-Formulation DL-23
Salicylic Acid Analysis By UV-VIS Method

| | Initial | 25° C. | 40° C. | 45° C. | 50° C. |
|---|---|---|---|---|---|
| 1.5 Month wt % | 0.924 | 0.964 | 0.952 | 0.942 | 0.941 |
| 2.0 Month, wt % | | 0.934 | 0.942 | 0.905 | 0.900 |

[1] Keltrol R is a xanthan gum obtained from Kelco Company
[2] Maltodextrin M040 is a hydrolyzed starch obtained from Grain Processing Corporation
[3] Pluronic F-108, is an ethoxylated/propoxylated block copolymer of propylene glycol obtained from BASF
[4] Tween 80 is a polyoxyethylene sorbitan ester of oleic acid obtained from Uniqema

TABLE 8

Barrier Film-Forming Compositions: Persistent Barrier Film and Germicidal Efficacy Evaluation

| Germicidal Efficacy Ingredients | DL-23 Wt % | DL-42 Wt % | DL-43 Wt % | DL-44 Wt % | DL-45 Wt % | DL-46 Wt % | DL-47 Wt % | DL-48 Wt % | DL-49 Wt % |
|---|---|---|---|---|---|---|---|---|---|
| Water | 72.11 | 77.36 | 76.96 | 76.31 | 75.01 | 73.36 | 74.36 | 74.86 | 72.86 |
| Keltrol R[1] | 0.40 | 0.40 | 0.40 | 0.40 | 0.40 | 0.40 | 0.40 | 0.40 | 0.40 |
| Sorbitol 70% | 14.29 | 14.29 | 14.29 | 14.29 | 14.29 | 14.29 | 14.29 | 14.29 | 14.29 |
| Maltrin M040[2] | 5.00 | 5.00 | 5.00 | 5.00 | 5.00 | 5.00 | 5.00 | 5.00 | 5.00 |
| Salicylic Acid | 0.90 | 0.90 | 0.90 | 0.90 | 0.90 | 0.90 | 0.90 | 0.90 | 0.90 |
| Allantoin | 0.10 | 0.10 | 0.10 | 0.10 | 0.10 | 0.10 | 0.10 | 0.10 | 0.10 |
| Lactic Acid (88%) USP | 4.00 | 0.00 | 0.50 | 1.00 | 2.00 | 3.00 | | | 2.00 |
| Iso Propyl Alcohol | | | | | | | 3.00 | 2.00 | 2.00 |
| Benzyl Alcohol | 1.00 | 1.00 | 1.00 | 1.00 | 1.00 | 1.00 | 1.00 | 1.00 | 1.00 |
| Pluronic F108[3] | 0.20 | 0.20 | 0.20 | 0.20 | 0.20 | 0.20 | 0.20 | 0.20 | 0.20 |
| Sodium Dioctylsulfosuccinate (75%) | 0.15 | 0.15 | 0.15 | 0.15 | 0.15 | 0.15 | 0.15 | 0.15 | 0.15 |
| Tween 80[4] | 0.30 | 0.30 | 0.30 | 0.30 | 0.30 | 0.30 | 0.30 | 0.30 | 0.30 |
| Sodium Hydroxide (50%) | 1.50 | 0.25 | 0.15 | 0.30 | 0.60 | 1.25 | 0.25 | 0.75 | 0.75 |
| FD&C Yellow 5-E102 | 0.03 | 0.03 | 0.03 | 0.03 | 0.03 | 0.03 | 0.03 | 0.03 | 0.03 |

TABLE 8-continued

Barrier Film-Forming Compositions: Persistent Barrier Film and Germicidal Efficacy Evaluation

| | | | | | | | | | |
|---|---|---|---|---|---|---|---|---|---|
| FD&C Blue 1-E133 | 0.02 | 0.02 | 0.02 | 0.02 | 0.02 | 0.02 | 0.02 | 0.02 | 0.02 |
| pH | 3.49 | 3.51 | 3.49 | 3.52 | 3.48 | 3.58 | 3.52 | 3.51 | 3.52 |
| Physical/Chemical Stability* | OK | PPT | PPT | Haze | OK | OK | Haze | PPT | PPT |

*Physical & Chemical stability was assessed at −15° C., 4° C., 25° C., 40° C., 45° C. and 50° C.;
Physical Instability is reported at precipitate (PPT), Haze and OK represents Physical and Chemical Stability under all temperatures conditions Germicidal Efficacy Data
EN 1656 Test: 25° C./30 Second: Log Reduction

| | Duplicate Runs | | Duplicate Runs | | | Duplicate Runs | | | | Duplicate Runs | | Duplicate Runs | | Duplicate Runs | |
|---|---|---|---|---|---|---|---|---|---|---|---|---|---|---|---|
| *E. Coli* | | | | | | | | | | | | | | | |
| Fresh Product | 7.0 | 7.0 | 7.1 | 7.1 | 7.1 | 7.1 | 7.1 | 7.1 | 7.1 | 7.0 7.1 | 7.1 7.1 | 7.0 7.1 | 7.1 7.1 | 7.0 7.1 | 7.1 7.1 |
| *Staph. Aureus* | | | | | | | | | | | | | | | |
| Fresh Product | 7.1 | 7.1 | 7.0 | 7.0 | 7.0 | 7.0 | 6.6 | 7.0 | 7.0 | 7.1 0 | 6.5 0 | 4.5 7.0 | 6.5 0 | 7.1 0 | 6.5 6.6 |

[1] Keltrol R is a xanthan gum obtained from Kelco Company
[2] Maltodextrin M040 is a hydrolyzed starch obtained from Grain Processing Corporation
[3] Pluronic F-108, is an ethoxylated/propoxylated block copolymer of propylene glycol obtained from BASF
[4] Tween 80 is a polyoxyethylene sorbitan ester of oleic acid obtained from Uniqema Example DL-50

Manufacturing Process

To mix the foregoing ingredients, water is charged into a mixing tank, and stirred to create a vortex. Keltrol R (xanthan gum) is added into the tank by slowly spreading into the vortex to facilitate quick mixing. Maintain a speed of the agitator for uniform mixing and for avoiding aeration. Continue mixing until the solution is homogeneous and no lumps are visible and present. Add liquid sorbitol and/or glycerin into the tank and mix for 5 minutes or until the mixture becomes homogeneous. Add maltodextrin M040 by dispersing slowly into the vortex and continue mixing until it is completely dissolved. Add salicylic acid by dispersing slowly into the vortex and continue mixing until it is completely dissolved. Add alantoin and pluronic F108 slowly and mix until they are completely dissolved and continue recirculation. Pump lactic acid, benzyl alcohol, sodium dioctylsulfo-succinate (Aerosol OT-75), Tween 80 and continue mixing until the solution is uniform and homogeneous. Pull sample from the bottom and top of the mixing tank and check for homogeneity. Add sodium hydroxide and continue mixing for about 20 minutes. Samples may be taken for measurement of pH and for analysis of lactic acid, benzyl alcohol and salicylic acid content. Adjust the pH of the solution to 3.50. Adjust the concentration of lactic acid, benzyl alcohol and salicylic acid if needed. Finally, coloring agents, such as FD&C Blue 1 and FD&C Yellow 5 are added into the mixing tank; mix 20 minutes or until all dyes dissolve in the solution. Samples may be taken to examine the existent of any lumps. If any lumps are observed, continue mixing until no lumps are visible.

Example DL-51

Antimicrobial Efficacy Studies

The teat dip formulation identified as the formula in Example DL-23 was subjected to a suspension test for evaluation of biocidal activity according to European Standard NF EN 1656 "Chemical disinfectants and antiseptics—Quantitative suspension test for the evaluation of bactericidal activity of chemical disinfectants and antiseptics used in veterinary field—Test method and requirements—(Phase 2, step 1)—April 2000. The principle of testing was to determine bactericidal activity in accordance with the reference strains *Enterococcus hirae* CIP 5855 and *Staphylococcus aureus* CIP 4 83. Test samples were stored at room temperature in darkness.

A dilution-neutralization solution was prepared according to Table 9.

TABLE 9

Dilution-Neutralization Solution.

| | |
|---|---|
| Lecithin: | 3 g |
| Polysorbate 80: | 30 g |
| Sodium thiosulphate: | 5 g |
| L-histidine chlorohydrate: | 1 g |
| Saponine: | 30 g |
| Distilled water: | Q.s.p. 500 ml. |
| Phosphate buffer 0.25 mol/l: | 10 ml. |
| Distilled water: | Q.s.p 1000 ml |
| Neutralizer added to the count medium: | 10% (v/v). |

Experimental Conditions:

Period of analysis: Six days

Product diluents used during the test: distilled water.

Product test concentrations: 5.0, 10.0, 20.0, 40.0, 80.0% (v/v) in sterile distilled water.

Test temperature: 30° C.+/−1° C.

Contact time: 30 minutes+/−10 seconds.

Interfering substance: 10 g/l of reconstituted milk.

Stability of the mixture (interfering substance and products): Precipitate absent throughout the tests.

Table 10 shows the experimental results confirming biocidal efficacy of the composition of the Example Temperature of incubation: 37° C.±1° C.

TABLE 10

Biocidal Efficacy of Composition of Example DL-23

| Test organisms: | Suspension A2 Nv | Validation tests. Experimental Conditions (30 min-30° C.) A | Neutralization control B | Inactivation by neutralization dilution C | Test procedure at concentration % (v/v) of: Bacterial test suspension N |
|---|---|---|---|---|---|
| Enterococcus hirae CIP 58 55 | Vc: 215; 252 A: $2.3 \cdot 10^3$ | Vc: 211; 256 B: $2.3 \cdot 10^2$ | Vc: 280; 243 A: $2.6 \cdot 10^2$ | Vc: 173; 149 C: $1.6 \cdot 10^2$ | $10^{-6}$: 242; 215 $10^{-7}$: 24; 31 N: $2.3 \cdot 10^8$ |
| Staphylococcus aureus CIP 4. 83 | Vc: 171; 199 Nv: $1.9 \cdot 10^3$ | Vc: 198; 201 A: $2.0 \cdot 10^2$ | Vc: 186; 198 B: $1.9 \cdot 10^2$ | Vc: 187; 173 C: $1.8 \cdot 10^2$ | $10^{-6}$: 190; 194 $10^{-7}$: 20; 20 N: $1.9 \cdot 10^8$ |

| Test organisms: | | Test procedure at concentration % (v/v) of: | | | | |
|---|---|---|---|---|---|---|
| | | 5.0 | 10.0 | 20.0 | 40.0 | 80.0 |
| Enterococcus hirae CIP 58 55 | Vc Na R | >300; >300 >$3.0 \cdot 10^3$ <$7.7 \cdot 10^3$ | >300; >300 >$3.0 \cdot 10^3$ <$7.7 \cdot 10^3$ | <15; <15 <$1.5 \cdot 10^2$ >$1.5 \cdot 10^5$ | <15; <15 <$1.5 \cdot 10^2$ >$1.5 \cdot 10^5$ | <15; <15 <$1.5 \cdot 10^2$ >$1.5 \cdot 10^5$ |
| Staphylococcus aureus CIP 4. 83 | Vc Na R | 104; 118 $1.1 \cdot 10^3$ $1.7 \cdot 10^4$ | 38; 39 $3.9 \cdot 10^2$ $4.9 \cdot 10^4$ | <15; <15 <$1.5 \cdot 10^2$ >$1.3 \cdot 10^5$ | <15; <15 <$1.5 \cdot 10^2$ >$1.3 \cdot 10^5$ | <15; <15 <$1.5 \cdot 10^2$ >$1.3 \cdot 10^5$ |

Vc: Viable count.
N: Number of cfu/ml of the bacterial test suspension (5.4.1.4.).
Nv: Number of cfu/ml of the bacterial suspension (A.2.).
Na: Number of cfu/ml in the test mixture (5.5.2.2.3. ou 5.5.2.3.3).
R: Reduction in viability (5.6.3.).
A: Number of cfu/ml of the experimental conditions validation (A.4.1.a ou A.4.2a).
B: Number of cfu/ml of the neutralizer toxicity validation (A.4.1.b) or of the filtration validation(A.4.2b).
C: Number of cfu/ml of the dilution-neutralization validation (A.4.1.c) or of the membrane filtration test validation (A.4.2c).

Conclusion:
According to NF EN 1656 (April 2000), in 30 minutes+/− 10 seconds of contact at 30° C., under 10 g/l of reconstituted milk, against the strains of *Enterococcus hirae* CIP 58 55 and *Staphylococcus aureus* CIP 4. 83, the product Experimental Teat Dip Formula in Example DL-23 diluted at 20.0% (v/v) possesses a bactericidal activity.

The same test was repeated using reference strains *Proteus vulgaris* CIP 5860 and *Pseudomonas aeruginosa* CIP 103467 according to NF EN 1656 (April 2000) in a five day study using an incubation temperature of 37° C.±1° C. Table 11 shows these results.

TABLE 11

Biocidal Efficacy of Composition of Example DL-23

| Test organisms: | Suspension A2 Nv | Validation tests. Experimental Conditions (30 min-30° C.) A | Neutralization control B | Inactivation by neutralization dilution C | Test procedure at concentration % (v/v) of: Bacterial test suspension N |
|---|---|---|---|---|---|
| Pseudomonas aeruginosa CIP 103467 | Vc: 254; 280 A: $2.7 \cdot 10^3$ | Vc: 218; 246 B: $2.3 \cdot 10^2$ | Vc: 282; 258 A: $2.7 \cdot 10^2$ | Vc: 208; 204 C: $2.1 \cdot 10^2$ | $10^{-6}$: 254; 226 $10^{-7}$: 23; 37 N: $2.5 \cdot 10^8$ |
| Proteus vulgaris CIP 5860 | Vc: 264; 266 Nv: $2.7 \cdot 10^3$ | Vc: 268; 284 A: $2.8 \cdot 10^2$ | Vc: 294; 275 B: $2.9 \cdot 10^2$ | Vc: 215; 224 C: $2.2 \cdot 10^2$ | $10^{-6}$: 252; 238 $10^{-7}$: 26; 41 N: $2.5 \cdot 10^8$ |

| Test organisms: | | Test procedure at concentration % (v/v) of: | | | | |
|---|---|---|---|---|---|---|
| | | 5.0 | 10.0 | 20.0 | 40.0 | 80.0 |
| Pseudomonas aeruginosa CIP 103467 | Vc Na R | >300; >300 >$3.0 \cdot 10^3$ <$8.3 \cdot 10^3$ | <15; <15 <$1.5 \cdot 10^2$ >$1.7 \cdot 10^5$ | <15; <15 <$1.5 \cdot 10^2$ >$1.7 \cdot 10^5$ | <15; <15 <$1.5 \cdot 10^2$ >$1.7 \cdot 10^5$ | <15; <15 <$1.5 \cdot 10^2$ >$1.7 \cdot 10^5$ |
| Proteus | Vc | >300; >300 | 37; 33 | <15; <15 | <15; <15 | <15; <15 |

TABLE 11-continued

| Biocidal Efficacy of Composition of Example DL-23 | | | | | | |
|---|---|---|---|---|---|---|
| vulgaris CIP 5860 | Na R | $>3.0 \cdot 10^3$ $<8.3 \cdot 10^3$ | $3.5 \cdot 10^2$ $7.1 \cdot 10^4$ | $<1.5 \cdot 10^2$ $>1.7 \cdot 10^5$ | $<1.5 \cdot 10^2$ $>1.7 \cdot 10^5$ | $<1.5 \cdot 10^2$ $>1.7 \cdot 10^5$ |

Vc: Viable count.
N: Number of cfu/ml of the bacterial test suspension (5.4.1.4.).
Nv: Number of cfu/ml of the bacterial suspension (A.2.).
Na: Number of cfu/ml in the test mixture (5.5.2.2.3. ou 5.5.2.3.3).
R: Reduction in viability (5.6.3.).
A: Number of cfu/ml of the experimental conditions validation (A.4.1.a ou A.4.2a).
B: Number of cfu/ml of the neutralizer toxicity validation (A.4.1.b) or of the filtration validation (A.4.2b).
C: Number of cfu/ml of the dilution-neutralization validation (A.4.1.c) or of the membrane filtration test validation (A.4.2c).

Conclusion:

According to NF EN 1656 (April 2000), in 30 minutes +/−10 seconds of contact at 30° C., under 10 g/l of reconstituted milk, against the strains of *Proteus vulgaris* CIP 5860 and *Pseudomonas aeruginosa* CIP 103467, the product Experimental Teat Dip of Example DL-23 diluted at 20.0% (v/v) possesses bactericidal activity.

The same test was repeated using Sample of Example DL-23 against reference strains *Enterococcus hirae* CIP 5855, *Proteus vulgaris* CIP 58.60, *Pseudomonas aeruginosa* CIP 103467, and *Staphylococcus aureus* CIP 4 83 *Proteus vulgaris* CIP 5860 and *Pseudomonas aeruginosa* CIP 103467 in a nine day study using an incubation temperature of 30° C.±1° C. Table 12 shows the results.

TABLE 12

| Biocidal Efficacy of Composition in Example DL-23 | | | | | |
|---|---|---|---|---|---|
| Test organisms: | Suspension A2 Nv | Validation tests. Experimental Conditions (5 min-30° C.) A | Neutralization control B | Inactivation by neutralization dilution C | Test procedure at concentration % (m/v) of: Bacterial test suspension N |
| *Enterococcus hirae* CIP 58 55 | Vc: 192; 222 A: $2.1 \cdot 10^3$ | Vc: 197; 202 B: $2.0 \cdot 10^2$ | Vc: 182; 240 A: $2.1 \cdot 10^2$ | Vc: 214; 202 C: $2.1 \cdot 10^2$ | $10^{-6}$: 208; 162 $10^{-7}$: 23; 15 N: $1.9 \cdot 10^8$ |
| *Proteus vulgaris* CIP 58.60 | Vc: 298; 292 Nv: $3.0 \cdot 10^3$ | Vc: 291; 286 A: $2.9 \cdot 10^2$ | Vc: 234; 246 B: $2.4 \cdot 10^2$ | Vc: 264; 292 C: $2.8 \cdot 10^2$ | $10^{-6}$: 201; 220 $10^{-7}$: 29; 21 N: $2.1 \cdot 10^8$ |
| *Pseudomonas aeruginosa* CIP 103467 | Vc: 234; 228 Nv: $2.3 \cdot 10^3$ | Vc: 264; 224 A: $2.4 \cdot 10^2$ | Vc: 252; 248 B: $2.5 \cdot 10^2$ | Vc: 218; 230 C: $2.2 \cdot 10^2$ | $10^{-6}$: 210; 228 $10^{-7}$: 24; 22 N: $2.2 \cdot 10^8$ |
| *Staphylococcus aureus* CIP 4. 83 | Vc: 242; 239 Nv: $2.4 \cdot 10^3$ | Vc: 231; 201 A: $2.2 \cdot 10^2$ | Vc: 226; 202 B: $2.1 \cdot 10^2$ | Vc: 198; 208 C: $2.0 \cdot 10^2$ | $10^{-6}$: 204; 240 $10^{-7}$: 21; 20 N: $2.2 \cdot 10^8$ |

| Test organisms: | | Test procedure at concentration % (m/v) of: | | | | |
|---|---|---|---|---|---|---|
| | | 5.0 | 10.0 | 20.0 | 40.0 | 80.0 |
| *Enterococcus hirae* CIP 58 55 | Vc Na R | >300; >300 >.,0 · $10^3$ <6.3 · $10^3$ | >300; >300 >3.0 · $10^3$ <6.3 · $10^3$ | >300; >300 >3.0 · $10^3$ <6.3 · $10^3$ | 31; 44 3.8 · $10^2$ 5.0 · $10^4$ | <15; <15 <1.5 · $10^2$ >1.3 · $10^5$ |
| *Proteus vulgaris* CIP 58.60 | Vc Na R | >300; >300 >3.0 · $10^3$ <7.0 · $10^3$ | 76; 93 8.5 · $10^2$ 2.5 · $10^4$ | <15; <15 <1.5 · $10^2$ >1.4 · $10^5$ | <15; <15 <1.5 · $10^2$ >1.4 · $10^5$ | <15; <15 <1.5 · $10^2$ >1.4 · $10^5$ |
| *Pseudomonas aeruginosa* CIP 103467 | Vc Na R | >300; >300 >3.0 · $10^3$ <7.3 · $10^3$ | <15; <15 <1.5 · $10^2$ >1.5 · $10^5$ | <15; <15 <1.5 · $10^2$ >1.5 · $10^5$ | <15; <15 <1.5 · $10^2$ >1.5 · $10^5$ | <15; <15 <1.5 · $10^2$ >1.5 · $10^5$ |
| *Staphylococcus aureus* CIP 4. 83 | Vc Na R | >300; >300 >3.0 · $10^3$ <7.3 · $10^3$ | >300; >300 >3.0 · $10^3$ <7.3 · $10^3$ | 130; 112 1.2 · $10^3$ 1.8 · $10^4$ | <15; <15 <1.5 · $10^2$ >1.5 · $10^5$ | <15; <15 <1.5 · $10^2$ >.5 · $10^5$ |

Vc: Viable count
N: Number of cfu/ml of the bacterial test suspension (5.4.1.4.).
Nv: Number of cfu/ml of the bacterial suspension (A.2.).
Na: Number of cfu/ml in the test mixture (5.5.2.2.3. ou 5.5.2.3.3).
R: Reduction in viability (5.6.3).
A: Number of cfu/ml of the experimental conditions validation (A.4.1.a ou A.4.2a).
B: Number of cfu/ml of the neutralizer toxicity validation (A.4.1.b) or of the filtration validation (A.4.2b).
C: Number of cfu/ml of the dilution-neutralization validation (A.4.1.c) or of the membrane filtration test validation (A.4.2c).

Conclusion:

According to NF EN 1656 (April 2000), in 5 minutes +/−10 seconds of contact at 30° C., under 10 g/l of reconstituted milk, against the strains of *Enterococcus hirae* CIP 58 55, *Proteus vulgaris* CIP 58.60, *Pseudomonas aeruginosa* CIP 103467, and *Staphylococcus aureus* CIP 4. 83, the product Experimental Teat Dip of Example DL-23 diluted at 80.0% (m/v) possesses a bactericidal activity.

An additional study was performed using the European standard NF EN 1040" Chemical disinfectants and antiseptics—Basic bactericidal activity—Test method and requirements (phase 1) April 1997 to test Sample of Example DL-23 of Table 5 against reference strains *Pseudomonas aeruginosa* CIP 103467 and *Staphylococcus aureus* CIP 4 83. The solution for dilution and neutralization was prepared according to Table 13.

TABLE 13

Solution for Dilution-Neutralization.

| | |
|---|---|
| Lecithin: | 3 g |
| Polysorbate 80: | 30 g |
| Sodium thiosulphate: | 5 g |
| L-histidine chlorohydrate: | 1 g |
| Saponine: | 30 g |
| Distilled water: | Q.s.p. 500 ml. |
| Phosphate buffer 0.25 mol/l: | 10 ml. |
| Distilled water: | Q.s.p 1000 ml |

Experimental Condition:
 Period of analysis: Ten days.
 Product test concentrations: 20.0, 40.0, 80.0% (w/v) in sterile distilled water.
 Test temperature: 20° C.+/−1° C.
 Contact time: 5 minutes +/−10 seconds.
 Temperature of incubation: 37° C.±1° C.
Tables 14 and 15 provide the results of this test.

TABLE 14

Verification of the Methodology and of the Dilution-Neutralization Validation for a Test Concentration of 80.0% (w/v) of the Product under Test.

| | Number of viable cells (UFC/ml): | | | |
|---|---|---|---|---|
| Strains: | Bacterial suspension test (N) | Bacterial suspension A.2 (Nv) | Toxicity of the neutralizer (Nx) | Dilution-neutralisation test (Ny) |
| *Pseudomonas aeruginosa* CIP 103467 | $2.8 \cdot 10^8$ | $2.9 \cdot 10^3$ | $2.7 \cdot 10^2$ | $2.9 \cdot 10^2$ |
| *Staphylococcus aureus* CIP 4 83 | $2.4 \cdot 10^8$ | $2.2 \cdot 10^3$ | $1.9 \cdot 10^2$ | $2.4 \cdot 10^2$ |

Validation requirements:

$1.5 \cdot 10^8 \leq N \leq 5 \cdot 10^8$ UFC/ml.

$6 \cdot 10^2 \leq Nv \leq 3 \cdot 10^3$ UFC/ml.

$Nx \geq 0.05 \times Nv$.

$Ny \geq 0.05 \times Nv$.

The neutralisation is validated for the tested neutralizer for a test concentration of 80.0% (w/v) of the product as received and for the strains under test.

TABLE 15

Actual Test Results (Dilution-Neutralization):

| | Number of viable cells (UFC/ml) in the test mixture (Na) in accordance with the concentrations in % (w/v): | | |
|---|---|---|---|
| Strains: | 20.0 | 40.0 | 80.0 |
| *Pseudomonas aeruginosa* CIP 103467 | $7.4 \cdot 10^2$ | $<1.5 \cdot 10^2$ | $<1.5 \cdot 10^2$ |
| *Staphylococcus aureus* CIP 4 83 | $<1.5 \cdot 10^2$ | $<1.5 \cdot 10^2$ | $<1.5 \cdot 10^2$ |
| Reduction of the number of viable cells at the tested concentrations: | | | |
| *Pseudomonas aeruginosa* CIP 103467 | $3.8 \cdot 10^4$ | $>1.9 \cdot 10^5$ | $>1.9 \cdot 10^5$ |
| *Staphylococcus aureus* CIP 4 83 | $>1.6 \cdot 10^5$ | $>1.6 \cdot 10^5$ | $>1.6 \cdot 10^5$ |

Conclusion:

In the specified operating conditions (5 minutes of contact at 20° C.) and for the sample under test, the Experimental Teat Dip composition of Example DL-23, has a basic bactericidal activity in accordance with the European standard NF EN 1040 (April 1997).

Example DL-52

Functional Comparison with Commercially Available Compositions

Continuous, uniform barrier films formed on the teat of cattle using the compositions disclosed herein and those used by other manufacturers were examined by an expert to assess their general quality as a barrier, durability, tendency to drip during application and their germicidal activity. Germicidal effects may be assessed, for example, as described above using a commercial testing service at Laboratoire Midac in France and Chemiphar in Belgium. Table 16 summarizes the results of such comparative studies, which demonstrate the superiority of the formulation from Example DL-23. Evaluation of physical and chemical attributes is well within the ordinary level of skill and may be done according to established methods.

TABLE 16

Comparison between the Present Barrier Film-forming composition and Some Commercial Products
Barrier Teat Dip Composition of Example DL-23 Features Against Commercial Products

| Product Attributes | Example DL-23 Value Added | Filmadine | Phytoshield | Ioshield | Uddergold Platinum |
|---|---|---|---|---|---|
| Manufacturer | DeLaval | Hypred-Europe | Ecolab-Europe | Ecolab-Europe | Ecolab-Europe |
| EU Product Registration | Medicinal | Non-Medicinal | Non-Medicinal | Non-Medicinal | Medicinal |
| Germicidal Properties | | | | | |
| Active Ingredients | Natural Ingredients Lactic Acid Salicylic Acid, Benzyl Alcohol | Lactic Acid | Natural Ingredients Plant Extracts | Iodine | $ClO_2$ Generated In-Situ |
| Germicidal Efficacy by AOAC Test | 7-8 log Reduction | 3-4 log Reduction | 3-4 log Reduction | 5 log Reduction | 5 log Reduction |
| Summary of Barrier/ Film Properties | | | | | |
| Barrier Agents | Surfactant/ Maltodextrin | | PVA | PVA | |
| Quality/Type | Excellent/Lotion Uniform Smooth Coating/Non-Peel able | Good/Lotion Non-Uniform/Gritty Film | Good/Very Thick Non-Uniform/Gritty Film Peel Able | Good/Very Thick Non-Uniform/Gritty Film Peel Able | Fair/Poor/Very Thin Non-Uniform/Gritty Film |
| Ease of Removal | Film Easy to Remove | Difficult When Dry | Difficult When Dry | Difficult When Dry | Easy |
| Vertical Cling/Retention (Adherence) | Non Dripping/ No Waste | Non Dripping/No Waste | Non Dripping/No Waste | Non Dripping/No Waste | Dripping —80% Waste |
| Residual Film (Persistent) | Visible up to 12 Hrs/ Uniform Film | Gritty Film/ Dull Color | Gritty Film/Dull Color | Gritty Film/Dull Color | Gritty Film/Dull Color |
| Durability in Water | Slowly Dissolves, Stays Longer | | Insoluble, Comes Off Quick | Insoluble, Comes Off Quick | |
| Film Quality (1-5 Scale, 5 = Best) | 4.0 | 4.0 | 5.0 | 5.0 | 4.0 |
| Product Adhered on Panel, gm | 0.319 | 0.173 | 0.352 | 0.118 | 0.032 |
| Emollient/Skin Conditioning Agent | 10% Sorbitol Allantoin/ Polysorbate | Glycerin (?) | 6% Glycerin | Glycerin 3%/Sorbitol 4% | 5% Glycerin |
| Product Physical Attributes | | | | | |
| Ease of Product Use | Excellent/RTU | Excellent/RTU | Fair/Very Viscous/RTU | Fair/Very Viscous/RTU | Fair/Two Parts/Not RTU |
| Product Visibility on Teats | Excellent | Excellent | Excellent | Good | Good |
| Product Physical Stability | Excellent | Good Some Separation@50° C. | Gel Irreversibly/Cold T Some Separation@50° C. | Gel Irreversibly/Cold T Lost Iodine Color to Yellow | Good Some Precipitation@50° C. |
| Viscosity, cPs (Brookfield LV2, 30 rpm at 25° C.) | 650-750 | 880 | 2200 | 2360 | 150 |
| Product Appearance | Translucent/ Homogen. | Opaque | Opaque Non-Homogen. | Opaque Homogeneous | Opaque Homogeneous |
| Color | Dark Bluish-Green | Homogeneous Red-Orange | Medium Light Green | Dark Brown-Iodine | Yellow |

Those skilled in the art will appreciate that the foregoing discussion teaches by way of example, and not by limitation. Insubstantial changes may be imposed upon the specific embodiments described here without departing from the scope and spirit of the invention.

We claim:

1. A method for treating an animal's teats to provide a protective germicidal barrier film between milkings, the method comprising: milking the animal; coating the teats with a teat dip product after milking; and allowing the dip product to dry and form a layer of film on said teats, wherein the teat dip product includes:
   a) from about 0.1% to about 20% by weight of a polysaccharide material having a majority amount of polysaccharide component that is determined on the basis of total polysaccharide material and is selected from the group consisting of modified starch, hydrolyzed starch, starch derivative and combinations thereof; the majority amount of polysaccharide component having on average an overall Dextrose Equivalence (DE) value ranging from 2 to 50;
   b) from about 0.1% to about 20% by weight of at least one antimicrobial active agent;
   c) a viscosity suitably adjusted to provide a viscosity ranging from 100 cPs to 4000 cPs; and
   d) at least one solvent constituting at least 50% by weight of the teat dip product.

2. The method of claim 1, wherein said teat dip further comprises from about 0.1% to about 20% by weight of at least one emollient or skin conditioning agent.

3. The method of claim 1, wherein the majority polysaccharide component has an overall Dextrose Equivalence (DE) value ranging from 3 to 27.

4. The method of claim 1, wherein the majority polysaccharide component is present in an amount comprising at least 1% of the composition weight.

5. The method of claim 1, wherein the majority polysaccharide component is selected from the group consisting of dextrin, maltodextrin, and combinations thereof.

6. The method of claim 5, wherein the majority polysaccharide comprises maltodextrin.

7. The method of claim 1, wherein the polysaccharide material consists essentially of the majority polysaccharide component.

8. The method of claim 1, wherein the polysaccharide material further includes a minority amount of cellulose determined on the basis of total polysaccharide material.

9. The method of claim 1, wherein the viscosity adjusting agent includes xanthan gum.

10. The method of claim 1, wherein the antimicrobial active agent includes a combination of organic acids and organic alcohols.

11. The method of claim 1, wherein the antimicrobial active agent induces at least one member selected from the group consisting of chlorohexidine digluconate and chlorohexidine diacetate, lactic acid, benzyl alcohol, salicylic acid, isopropyl alcohol, organic peroxide, hydrogen peroxide, peroxy acids, bronopol (2-bromo-2-nitro-1,3-propanediol), salicylic acid, polyhexamethylenebiguamide, quaternary ammonium compounds, chlorine dioxide, hypohalous acid, alkali hypohalites, chlorine dioxide precursors, and mixtures thereof.

12. The method of claim 1, wherein said teat dip product futher includes an additive selected from the group consisting of a buffering agent, a pH adjusting agent, an emollient, a preservative, a moisturizing agent, a skin conditioning agent, a surfactant or wetting agent, a viscosity control agent, a colorant, an opacifying agent and combinations thereof.

13. The method of claim 1, wherein said teat dip product further comprises from about 0.001% to about 5.00% (w/w) of a coloring agent.

14. The method of claim 1, wherein said composition has a pH ranging from about 2.0 to about 9.0.

15. A method for treating or preventing mastitis, comprising causing the skin of a subject in need of a prophylactic treatment to be in contact with a teat dip product comprising:
   a) from about 0.1% to about 20% by weight of a polysaccharide material having a majority amount of polysaccharide component that is determined on the basis of total polysaccharide material and is selected from the group constisting of modified starch, hydrolyzed starch, starch derivative and combinations thereof; the majority amount of polysaccharide component having on average an overall Dextrose Equivalence (DE) value ranging from 2 to 50;
   b) from about 0.1% to about 20% by weight of at least one antimicrobial active agent;
   c) a viscosity suitably adjusted to provide a viscosity ranging from 100 cPs to 4000 cps; and
   d) at least one solvent constituting at least 50% by weigth of the teat dip product.

16. A method of claim 15, wherein the subject is an animal.

17. The method of claim 16, wherein the teat dip product is applied topically to the skin of the animal's teats.

18. The method of claim 17, wherein the teat dip product is applied to the teats of the animal by paint brushing, foaming, dipping or spraying.

\* \* \* \* \*